(12) United States Patent
von Recum et al.

(10) Patent No.: US 9,931,404 B2
(45) Date of Patent: Apr. 3, 2018

(54) GLYCOSAMINOGLYCANS FOR CHEMOKINE DRUG DELIVERY

(71) Applicant: Case Western Reserve University, Cleveland, OH (US)

(72) Inventors: Horst A. von Recum, Cleveland Heights, OH (US); Adonis Hijaz, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/300,641

(22) Filed: Jun. 10, 2014

(65) Prior Publication Data

US 2014/0364360 A1 Dec. 11, 2014

Related U.S. Application Data

(60) Provisional application No. 61/833,048, filed on Jun. 10, 2013, provisional application No. 61/859,617, filed on Jul. 29, 2013.

(51) Int. Cl.
| | |
|---|---|
| *A61K 47/36* | (2006.01) |
| *A61K 47/42* | (2017.01) |
| *A61K 38/19* | (2006.01) |
| *A61K 9/00* | (2006.01) |

(52) U.S. Cl.
CPC ............ *A61K 47/36* (2013.01); *A61K 9/0036* (2013.01); *A61K 38/195* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 2007/0081976 A1* | 4/2007 | Cohen et al. | ................ 424/85.6 |
| 2012/0100185 A1* | 4/2012 | Wen | ..................... A61L 27/227 424/400 |
| 2012/0220518 A1 | 8/2012 | von Recum et al. | |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Prokoph et al (Biomaterials 33 (2012) 4792-4800; published online Apr. 6, 2012).*
Duo et al (Anal Bioanal Chem (2011) 399:773-782).*
Lau et al (The Journal of Biological Chemistry, 279, 22294-22305).*
Kuschert (Biochemistry. Sep. 28, 1999;38(39):12959-68).*
NCBI entry for CXCL12 (downloaded from https://www.ncbi.nlm.nih.gov/gene/6387 on May 7, 2017).*
Baumann et al (Journal of Controlled Release 162 (2012) 68-75).*
Elisseeff (Nature Materials 7, 271-273 (2008)).*
Bendall "Chemokines and Their Receptors in Disease", Histology and Histopathology, 2005, vol. 20, pp. 907-926.
Brandner et al., "Engineering the Glycosaminoglycan-Binding Affinity, Kinetics and Oligomerization Behavior of RANTES: A Tool for Generating Chemokine-Based Glycosaminoglycan Antagonists", Protein Engineering, Design & Selection, 2009, vol. 22, No. 6, pp. 367-373.
Cruz et al., "Pelvic Organ Distribution of Mesenchymal Stem Cells Injected Intravenously After Simulated Childbirth Injury in Female Rats", Obstetrics and Gynecology International, 2012, pp. 1-7.
Dissaranan et al., "Rat Mesenchymal Stem Cell Secretome Promotes Elastogensis and Facilitates Recovery from Simulated Childbirth Injury", Cognizant Communication Corporation, 2013, pp. 1-32.
Duo et al., "Heparin-Immobilized Microspheres for the Capture of Cytokines", Anal Bioanal Chem, 2011, vol. 399, pp. 773-782.
Duo et al., "In Vitro and In Vivo Affinity Microdialysis Sampling of Cytokines Using Heparin-Immobilized Microspheres", Anal Bioanal Chem., 2011, vol. 399(2), pp. 1-21.
Fehske et al., "The Location of Drug Binding Sites in Human Serum Albumin" Biochemical Pharmacology, 1981, vol. 30, No. 7, pp. 687-692.
Gaertner et al., "Highly Potent, Fully Recombinant Anti-HIV Chemokines: Reengineering a Low-Cost Microbicide" PNAS, 2008, vol. 105, No. 46, 17706-17711.
Howard, "Delivery of RNA Interference Therapeutics Using Polycation-Based Nanoparticles", Advanced Drug Delivery Reviews, 2009, vol. 61, pp. 710.720.
Kean et al., "MSC's Delivery Routes and Engraftment, Cell-Targeting Strategies, and Immune Modulation", Stem Cells International, 2013, pp. 1-13.
Kim et al., "Bone-Marrow-Derived Mesenchymal Stem Cell Transplantation Enhances Closing Pressure and Leak Point Pressure in a Female Urinary Incontinence Rat Model", Urol Int., 2011, vol. 86, pp. 110-116.
Marquez-Curtis et al., "Enhancing the Migration Ability of Mesenchymal Stromal Cells by Targeting the SDF-1/CXCR4 Axis", BioMed Research International, 2013, pp. 1-15.
Maxwell et al., "Development of Rationally Designed Affinity-Based Drug Delivery Systems" Acta Biomaterialia, 2005, pp. 101-113.
von Recum et al., "Growth Factor and Matrix Molecules Preserve Cell Function on Thermally Responsive Culture Surfaces" Tissue Engineering, 1999, vol. 5, No. 3, pp. 251-265.
Sakiyama-Elbert et al., "Development of Fibrin Derivatives for Controlled Release of Heparin-Binding Growth Factors", Journal of Controlled Release, 2000, vol. 65, pp. 389-405.
Schenk et al., "Monocyte Chemotactic Protein-3 is a Myocardial Mesenchymal Stem Cell Homing Factor", Stem Cells, 2007, vol. 25, pp. 245-251.

(Continued)

*Primary Examiner* — Brian Gangle
*Assistant Examiner* — Andrea K McCollum
(74) *Attorney, Agent, or Firm* — Tarolli, Sundheim, Covell & Tummino LLP

(57) ABSTRACT

A pharmaceutical composition for sustained release of a chemokine is described that includes a polymer bonded to a sulfated glycosaminoglycan and loaded with a chemokine having affinity for the sulfated glycosaminoglycan. The pharmaceutical composition can be used in a method for providing sustained release of a chemokine to subject by contacting the subject with the pharmaceutical composition.

16 Claims, 11 Drawing Sheets

(56) References Cited

OTHER PUBLICATIONS

Shute, "Glycosaminoglycan and Chemokine/Growth Factor Interactions", Handbook of Experimental Pharmacology, 2012, 207, pp. 307-324.
Lin et al., "Stem Cell Therapy for Stress Urinary Incontinence: A Critical Review", Stem Cells and Development, 2012, vol. 21, pp. 834-843.
Shinohara et al., "Stromal Cell-Derived Factor-1 and Monocyte Chemotactic Protein-3 Improve Recruitment of Oteogenic Cells into Sites of Musculoskeletal Repair", Journal of Orthopaedic Research, 2011, pp. 1064-1069.
Wang et al., "Affinity-Based Drug Delivery", Macromol. Biosci., 2011, vol. 11, pp. 321-332.
Thatiparti et al., "Cyclodextrin Complexation for Affinity-Based Antibiotic Delivery", Macromol. Biosci., 2010, vol. 10, pp. 82-90.
Wei et al., "Recent Advances on Noncovalent Molecular Imprints for Affinity Separations", J. Sep. Sci, 2007, vol. 30, pp. 1794-1805.
Wood et al., "Cytokine Expression After Vaginal Distension of Different Durations in Virgin Sprague-Dawley Rats", K. Urol., 2008, vol. 180(2), pp. 753-759.

* cited by examiner

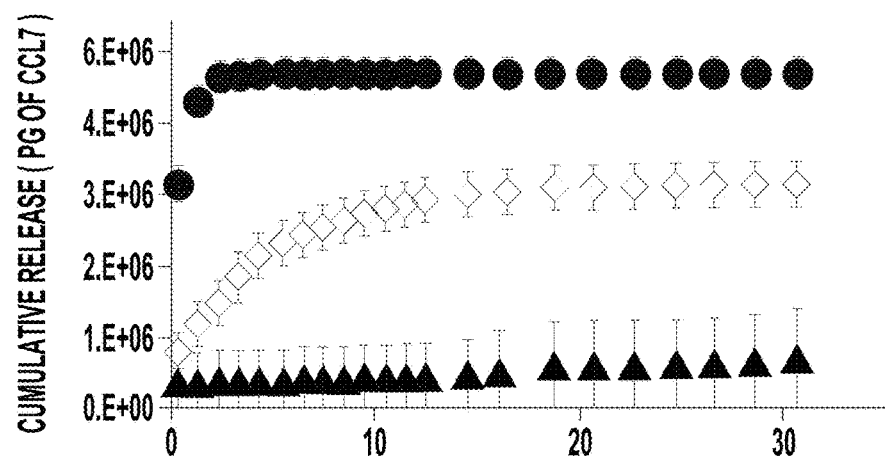
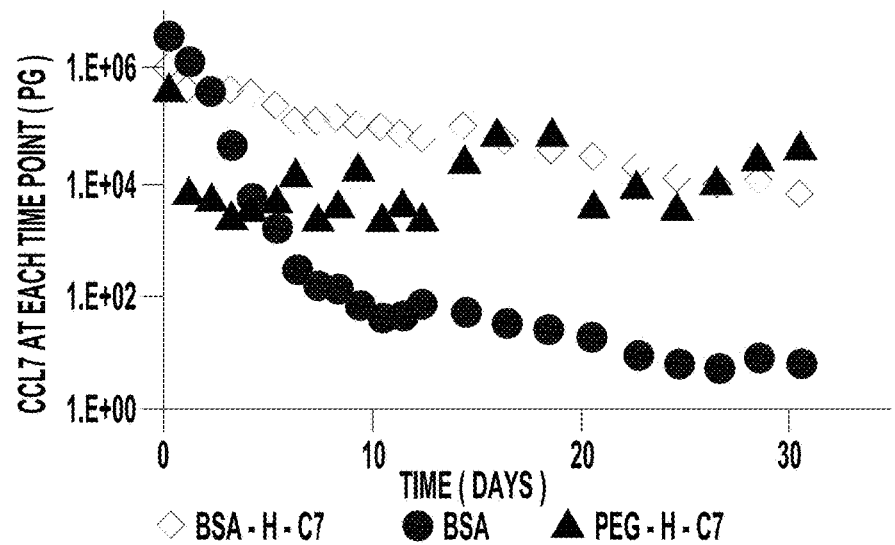
FIG. 12

GLYCOSAMINOGLYCANS FOR CHEMOKINE DRUG DELIVERY

CROSS-REFERENCE TO RELATED APPLICATIONS

This application claims the benefit of U.S. Provisional Application Ser. No. 61/833,048, filed Jun. 10, 2013, and U.S. Provisional Application Ser. No. 61/859,617, filed Jul. 29, 2013, the disclosures of which are incorporated by reference herein.

STATEMENT REGARDING FEDERALLY SPONSORED RESEARCH

This work was supported, at least in part, by grant number CBET-0954489 from the National Science Foundation, grant number U19-AI-868981-01 from the National Institute of Allergy and Infectious Disease, National Institutes of Health, and grant number T32DK091213 from the National Institute of Diabetes and Digestive and Kidney Diseases, National Institutes of Health. The United States government has certain rights in this invention.

BACKGROUND

Affinity-based drug delivery is a class of delivery systems that has recently gained popularity. These systems intentionally incorporate affinity moieties that interact with the agent of interest to control and manipulate its loading and release. Drug release rates from these systems are governed by the kinetic parameters in binding and release between the drug and the affinity moieties within the delivery systems, not by diffusion alone. As a result, release can be tailored based on the strength of these interactions. Affinity-based drug delivery systems have been used in the delivery of antibiotics, chemotherapy agents and growth factors. Wang, N. X.; von Recum, H., Macromol Biosci 11(3), 321-32 (2011); Maxwell et al., Acta Biomater 1(1), 101-13 (2005). The affinity used in drug delivery systems can be based on numerous interactions, including charge, hydrophobicity, and van der Waals forces.

Examples of affinity-based drug delivery systems include polycations, albumin, cyclodextrins, molecular imprinting, and heparin binding. Polycations are typically used for administering nucleic acids K. A. Howard, Adv. Drug Delivery Rev. 61, 710 (2009). Albumin has a high affinity for metal ions, fatty acids, amino acids, and numerous drug compounds. Fehske et al., Biochem. Pharmacol. 30, 687 (1981). Cyclodextrins are cyclic oligosaccharides that enable cyclodextrins to complex with small hydrophobic drugs and or molecules, and is typically used to increase hydrophilicity. A hydrogel including β-cyclodextrin with isocyanate crosslinking has been developed for delivering antibiotics. T. R. Thatiparti, H. A. von Recum, Macromol. Biosci. 10, 82 (2010). Molecular imprinting is a method use to form biomimetic polymer networks with template-shaped cavities that increase affinity for specific molecules of interest. Because of readily adaptable and rapid synthesis, close resemblance to molecular recognition, and availability of functional monomer libraries, use of non-covalent interactions has proven to be the most popular. S. Wei, B. Mizaikoff, J. Sep. Sci. 30, 1794 (2007). After establishing a non-covalent interaction between functional monomers and the template of choice, the monomers are polymerized with the template molecule still present, after which the template molecule is remove, leaving behind a template shaped cavity with affinity for the molecule of interest. E. Oral, N. A. Peppas, J. Biomed. Mater. Res., A 78, 205 (2006).

Heparan sulfate is a naturally occurring, highly sulfated anionic glycosaminoglycan found in the extracellular matrix that is responsible for immobilizing and releasing various proteins that influence natural processes such as cell adhesion, migration, proliferation, and differentiation. The specific heparin binding domain on numerous growth factors is highly specific and can interaction with heparin via non-covalent interactions. S. E. Sakiyama-Elbert, J. A. Hubbell, J. Controlled Release 65, 389 (2000). RANTES and its derivatives are known to have affinity interactions with various glycosaminoglycans (GAGs), with heparin having the strongest affinity, followed by various chondroitin sulfates (von Recum et al., Tissue Eng 5(3), 251-65 (1999) and uncleaved heparan sulfates. Brandner et al., Protein Eng Des Sel, 22(6), 367-73 (2009). These interactions have been explored in the application of biosensor and diagnostic development for cytokines. Duo et al., Anal Bioanal Chem, 399(2), 773-82 (2011); Duo, J.; Stenken, J. A., Anal Bioanal Chem., 399(2), 783-93 (2011).

SUMMARY

RANTES is a recently discovered chemokine that has shown high level protection from SHIV infection in macaques. However, the feasibility of using RANTES as a long term HIV prevention agent has not been explored partially due to its short half-life and the lack of available delivery devices that can easily be modified for long-term release profiles. Analogs of RANTES with longer halflives or longer mechanism of action, such as 5P12-RANTES have been explored, but even those require a delivery mechanism to provide therapeutic benefit beyond a few days. Glycosaminoglycans (GAGs) have been known for their affinity for various cytokines and chemokines, including native RANTES, or CCL5. In this work, the use of GAGs in generating a chemokine drug delivery device was investigated. Initial studies used surface plasmon resonance analysis to characterize and compare the affinities of different GAGs to RANTES and its analogs, such as 5P12-RANTES. These different GAGs were then incorporated into drug delivery polymeric hydrogels to engineer sustained release of the chemokines. In vitro release studies of RANTES analogs from the resulting polymers were performed and it was found that RANTES analog release from these polymers can be controlled by the amount and type of GAG incorporated. Polymer disks containing GAGs with stronger affinity to RANTES analogs resulted in more sustained, and longer term release than did polymer disks containing GAGs with weaker RANTES analog affinity. Similar trends were observed by varying the amount of GAGs incorporated into the delivery system. RANTES analogs released from these polymers demonstrated good levels of CCR5 blocking, retaining activity even after 30 days of incubation.

In addition, the inventors evaluated use of the invention for the treatment of urinary incontinence. The protein chemokine (C-C motif) ligand 7 (CCL7) is significantly over expressed in urethral and vaginal tissues immediately following induction of a rat model of stress urinary incontinence. Evidence indicates the CCL7 potently stimulates stem cell migration for regenerative repair. As a potential therapy, the effect of exogenous CCL7 delivery on the in vivo migration of human mesenchymal stem cells (hMSC) was examined in a rat model. To show that CCL7 recruits locally injected hMSC and inhibits injection site exodus, polymer blends containing heparin were designed for the controlled release of CCL7. The inventors took advantage of the binding affinity between chemokines and sulfated proteoglycans to engineer a polymer that allowed for sustained release of CCL7 beyond that capable of systems relying on diffusion alone. In vitro release experiments indicate the addition of heparin to a polymer blend, using either poly (ethylene glycol) or bovine serum albumin as an inert co-polymer, show sustained local concentrations of CCL7 in the range in a therapeutically useful range up to a month post implantation. Cryoimaging data of the CCL7 loaded affinity polymers show hMSC injury site retention.

In one aspect, the present invention provides a pharmaceutical composition for sustained release of a chemokine. The pharmaceutical composition includes a polymer bonded to a sulfated glycosaminoglycan and loaded with a chemokine having affinity for the sulfated glycosaminoglycan. In some embodiments, the polymer is included in a preformed device, such as a polymeric ring, or microparticles. In other embodiments, the polymer is a gel, such as a hydrogel. Suitable chemokines for use in different embodiments include CCL5 and CCL7.

The polymer used in the composition can be varied in a number of different ways. In some embodiments, the polymer includes an albumin (e.g., bovine serum albumin). In other embodiments, the polymer is crosslinked with a plurality of types of sulfated glycosaminoglycans. In further embodiments, the one or more of the sulfated glycosaminoglycans are selected from the group consisting of heparan sulfate, heparin (a fragment of heparin sulfate), chondroitin sulfate A, and chondroitin sulfate B.

Other aspects of the invention include methods of using the pharmaceutical composition. For example, one aspect provides a method for providing sustained release of a chemokine to subject that includes contacting the subject with the pharmaceutical composition. Another aspect provides a method for preventing infection of a female mammalian subject by a sexually transmitted disease that includes contacting the subject with a pharmaceutical composition including a chemokine that is effective for treating the sexually transmitted disease (e.g., infection by human immunodeficiency virus). Yet another aspect provides a method of treating an injury in a subject in need thereof that includes positioning a pharmaceutical composition described herein proximal to the injury that includes a chemokine that is effective for attracting host stem cells, such as mesenchymal stem cells to the injury. In some embodiments, the injury is a result of stress urinary incontinence.

BRIEF DESCRIPTION OF THE FIGURES

The present invention may be more readily understood by reference to the following drawings, wherein:

FIGS. 11A-11D provide graphs showing the results of an affinity determination between CCL7 and sulfated proteoglycans. CCL7 interaction sensorgrams on an SPR, with increasing concentrations of different sulfated proteoglycans. (A) shows heparin (12.5 nM-250 nM). (B) shows heparan sulfate (12.5 nM-250 nM). (C) shows chondroitin sulfate A (0.8 uM-8 uM). (D) Table summary of the different calculated dissociation constants from the above SPR experiments.

FIGS. 12A and 12B provide graphs showing the release profiles of CCL7 from different polymer formulations. 12A shows cumulative release, 12B shows release measured at each time point. BSA (●) shows a rapid burst over 5 days, with a low rate (<100 pg/day) after that. BSA-Heparin (◇) and PEG-Heparin (▲) show a decreased burst, followed by a sustained rate of ~10,000 pg/day. 12B is a replot of the same data, confirming burst and sustained rates, and indicating a difference of 4 orders of magnitude in rate.

FIGS. 13A-13D provide images showing BSA-H and PEG-H polymer implantation, integration, and excision in rat model. The polymers were implanted peri-urethrally in the anterior wall of vagina. Implant integration was evaluated 3 weeks after surgery. (C) Location of BSA-H and PEG-H implants during excision. PEG-H implant shows tissue adhesion (upper right), while BSA implant was found, unadhered in a pocket of connective tissue (lower right). (D) Excised implants showing tissue adhesion to PEG-H polymer, and little adhesion to BSA-H polymer.

FIGS. 14A and 14B provide graphs showing the determination of human CCL7 content in rat urethral tissue after two weeks of delivery. (A) shows the individual concentrations of the human chemokine in pg of CCL7/mL of sample, as determined by ELISA. Non-loaded polymers (BSA-H) show basal detection at $10^{-8}$ pg/ml. BSA-H polymers loaded with drug (BSA-H-C7) show an order of magnitude higher ($10^{-7}$ pg/ml). PEG-H polymers loaded with drug (PEG-H-C7) show as much as three orders of magnitude increase ($10^{-5}$ pg/ml). (B) is a plot of this relative difference compared to the baseline of unloaded polymers (BSA-H).

FIGS. 15A1-15B provide images showing stem cell retention in a rodent model following sustained CCL7 delivery. After 2 weeks of delivery, fluorescently labelled, human mesenchymal stem cells were injected periurethrally, and cell migration out of the injection site was evaluated by whole animal serial sectioning (cryoimaging). The timeline of experiments was as it follows: Day 0: implantation of CCL7 delivery device (B) and non-loaded controls (A), Day 12: Periurethral injection of 1.5 million hMSC, Day 13: Cryoimaging and fluorescence microscopy. A-1, A-2) Two different sections of non-loaded BSA-H polymer controls, showing diffusion of hMSCs away from the injection site and an overall decrease in signal intensity. B) CCL7-loaded BSA-H polymer showed highly localized retention of MSCs, and a high intensity signal at the injection site without any indication of cell diffusion away from the injection site. (Due to their different position within a frozen block, there is a slight rotation between cryoimaged animals, but both are still imaged supine.)

DETAILED DESCRIPTION

Figure 1:
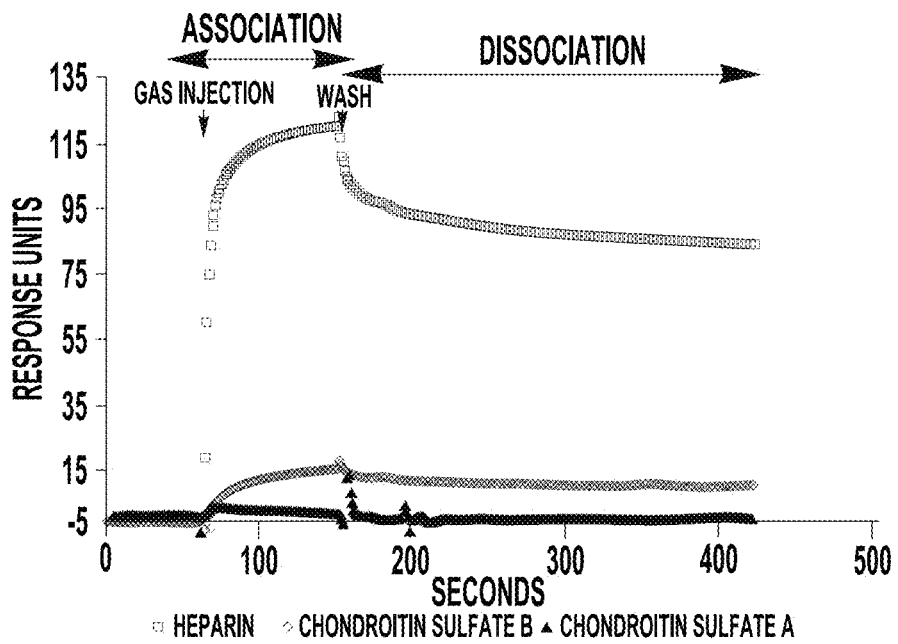
FIG. 1 is a graph showing an SPR analysis of GAGs (heparin, CSA and CSB) interactions with immobilized 5P12-RANTES. Overlaid sensorgrams show initial background wash (1 min), followed by injection of GAG solution and association of GAGs with the immobilized 5P12-RANTES on the chip surface over the following 1.5 min, and then subsequent washing (dissociation) of GAGs from the surface for the remaining 4.5 min.
Figure 2:
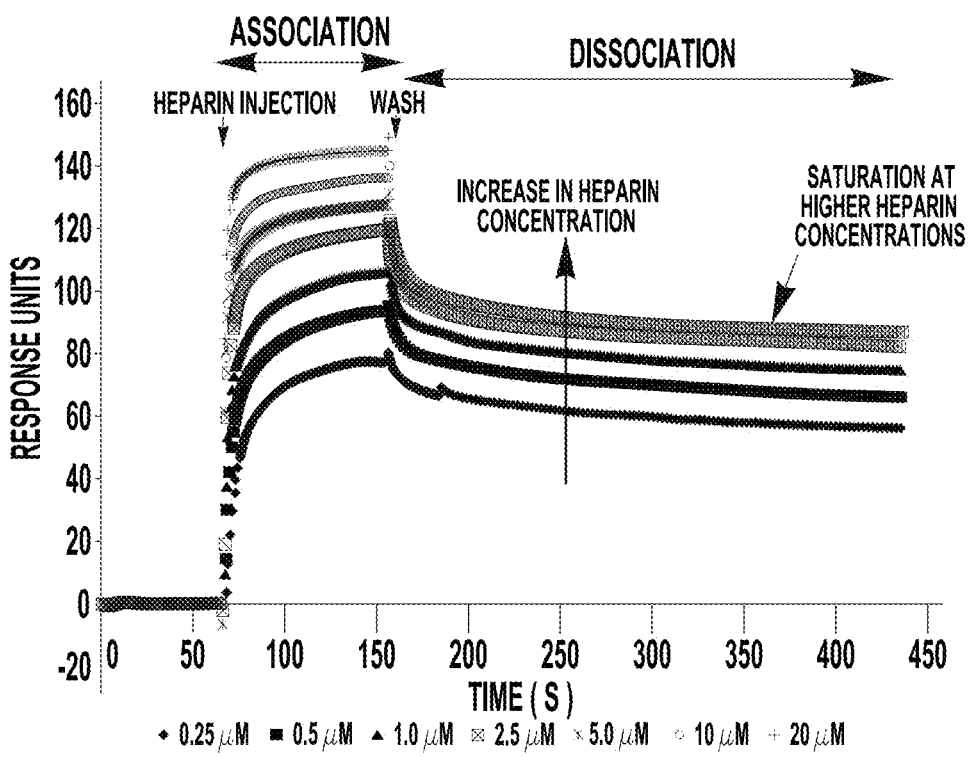
FIG. 2 is a graph showing an SPR concentration analysis of heparin/5P12-RANTES interactions. Overlaid sensorgrams showing initial background wash (1 min), followed by injection of heparin at 0.25, 0.5, 1.0, 2.5, 5.0, 10 and 20 FM for the next 1.5 min, and then subsequent washing (dissociation) of heparin from the surface for the remaining 4.5 min.
Figure 3:
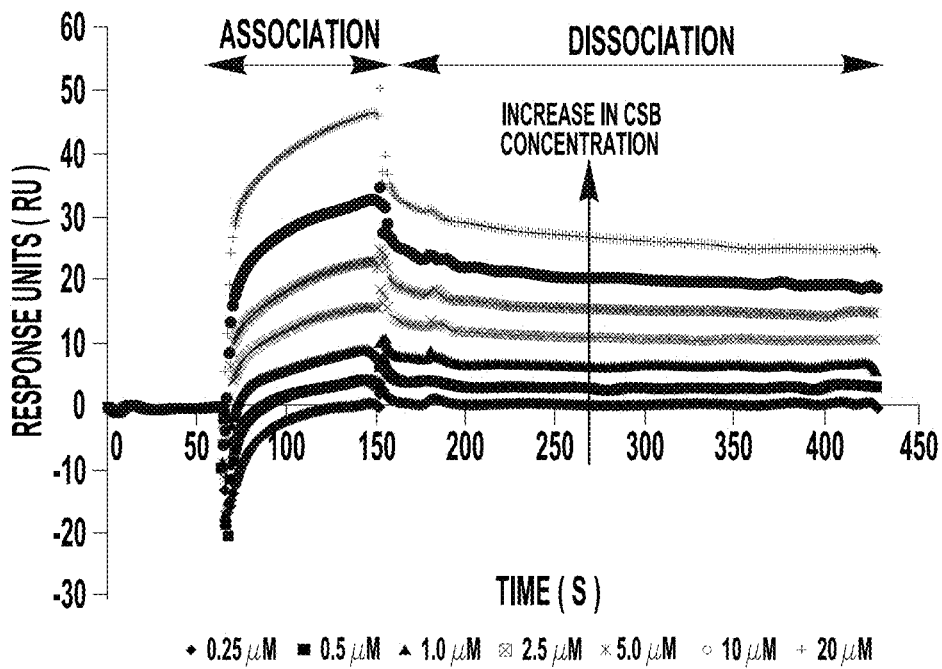
FIG. 3 is a graph showing an SPR concentration analysis of CSB/5P12-RANTES interactions. Overlaid sensorgrams showing initial background wash (1 min), followed by injection of heparin at 0.25, 0.5, 1.0, 2.5, 5.0, 10 and 20 FM for the next 1.5 mins, and then subsequent washing (dissociation) of CSB from the surface for the remaining 4.5 min.
Figure 4:
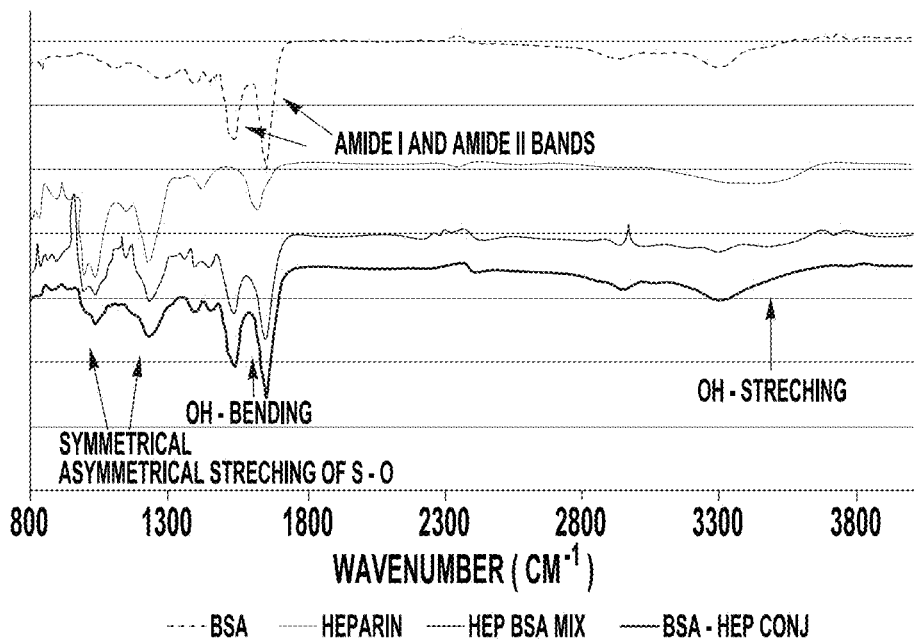
FIG. 4 is a graph showing an FTIR of BSA, heparin, heparin mixed with BSA (no conjugation) and crosslinked heparin/BSA. The spectra of crosslinked BSA and heparin occurred after multiple, extensive washings. The presence of both BSA and heparin confirm that crosslinking occurred. Small changes in OH groups indicate that conjugation could be through coupling to the GAG carboxylate.

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such. In addition, the recitations of numerical ranges by endpoints include all numbers subsumed within that range (e.g., 1 to 5 includes 1, 1.5, 2, 2.75, 3, 3.80, 4, 5, etc.).

"Treat", "treating", and "treatment", etc., as used herein, refer to any action providing a benefit to a subject afflicted with a condition or disease such as a sexually transmitted disease, including improvement in the condition through lessening or suppression of at least one symptom, delay in progression of the disease, etc.

Prevention, as used herein, refers to any action providing a benefit to a subject at risk of being afflicted with a condition or disease such as a sexually transmitted disease, including avoidance of the development of the disease or a decrease of one or more symptoms of a disease should one develop. The subject may be at risk due, for example, to exposure to the disease.

"Pharmaceutically acceptable" as used herein means that the compound or composition is suitable for administration to a subject for the methods described herein, without unduly deleterious side effects in light of the severity of the disease and necessity of the treatment. A pharmaceutical composition, as used herein, refers to a composition that is pharmaceutically acceptable.

"Biocompatible" as used herein, refers to a material (e.g., a pharmaceutical composition) that does not cause injury or death to the subject or induce an adverse reaction in a subject when placed in contact with the subject. Adverse reactions include for example inflammation, infection, fibrotic tissue formation, cell death, or thrombosis. The terms "biocompatible" and "biocompatibility" when used herein are art-recognized and mean that the referent is neither itself toxic to the subject, nor degrades (if it degrades) at a rate that produces byproducts (e.g., monomeric or oligomeric subunits or other byproducts) at toxic concentrations, does not cause prolonged inflammation or irritation, or does not induce more than a basal immune reaction in the subject.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

As used herein, the term "affinity" refers to the tendency of a compound to naturally associate with a region on the surface of a protein. Affinities are influenced by non-covalent intermolecular interactions between the two molecules such as hydrogen bonding, electrostatic interactions, hydrophobic and Van der Waals forces. The level of affinity is expressed by a dissociation constant, which has molar units (M) that correspond to the concentration of ligand at which the site of affinity on a particular protein is half occupied, i.e.

the concentration of ligand, at which the concentration of protein with ligand bound, equals the concentration of protein with no ligand bound. The smaller the dissociation constant, the more tightly bound the ligand is, or the higher the affinity between ligand and protein. As used herein, a compound can be said to have affinity for a protein if it would have dissociation constant of at least one micromolar.

As used herein, "polypeptide" refers to a polymer of amino acids and does not imply a specific length of a polymer of amino acids. Thus, for example, the terms peptide, oligopeptide, protein, antibody, and enzyme are included within the definition of polypeptide. This term also includes polypeptides with post-expression modification, such as glycosylation (e.g., the addition of a saccharide or polysaccharide), acetylation, phosphorylation, and the like.

Glycosaminoglycans (GAGs), as the term is used herein, are long unbranched polysaccharides consisting of a repeating disaccharide unit. The repeating unit generally consists of an amino sugar (e.g., N-acetylglucose amine or N-acetylgalactose amine) along with a uronic sugar (e.g., glucuronic acid or iduronic acid) or galactose. Sulfated glycosaminoglycans are glycosaminoglycans that include sulfate groups. Examples of sulfated glycosaminoglycans include heparin and chondroitin sulfate.

In one aspect, the invention provides a pharmaceutical composition for sustained release of a chemokine that includes a polymer bonded to a sulfated glycosaminoglycan and loaded with a chemokine having affinity for the sulfated glycosaminoglycan.

Chemokines are a family of cytokines, or signaling proteins secreted by cells, and include homeostatic chemokines and inflammatory chemokines. All chemokines are small, with a molecular mass of between 8 and 10 kDa. They are approximately 20-50% identical to one another and possess conserved amino acids that are important for creating their 3-dimensional or tertiary structure. Classes of chemokines included CC chemokines, CXC chemokines, C chemokines, and CX3C chemokines. In some embodiments, the pharmaceutical composition includes CC chemokines. CC chemokines have two adjacent cysteines (amino acids), near their amino terminus. There have been at least 27 distinct members of this subgroup reported for mammals, called CC chemokine ligands, which therefore include CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28, with CCL9 and CCL10 being identical. Chemokine ligands bind to their corresponding receptors; e.g., CCL5 binds to CCR5. An example of a CXC chemokine is CXL12. Examples of CC chemokine include monocyte chemoattractant protein-1 (MCP-1 or CCL2) which induces monocytes to leave the bloodstream and enter the surrounding tissue to become tissue macrophages, CCL5 (or RANTES) that attracts cells such as T cells, eosinophils and basophils that express the receptor CCR5, and CCL7, which attracts monocytes and mesenchymal stem cells, and regulates macrophage function. Accordingly, in some embodiments the chemokine is CCL5 (i.e., a CCR5 ligand). In further embodiments, the chemokine is a CCL5 analog, such as 5P12-RANTES. In other embodiments, the chemokine is CCL7 (i.e., a CCR7 ligand).

Chemokines have an affinity for the sulfated glycosaminoglycan, and this affinity provides for sustained release of the chemokine from the pharmaceutical composition, which includes sulfated glycosaminoglycan. When the pharmaceutical composition is administered or placed in contact with a biological fluid (such as serum, synovial fluid, cerebral spinal fluid, lymph, urine, etc.) or a tissue or injury site, the composition provides a sustained release of the glycosaminoglycan. In certain embodiments, the duration of release from the pharmaceutical composition is at least 3 hours, and even more preferably may be at least 24, 72, 100, 250, 500 or even 750 hours. In certain embodiments, the duration of release of the chemokine from the composition is at least one week, more preferably two weeks, or at least three weeks. In certain embodiments, the duration of release of the agent from the polymer matrix is at least one month, more preferably at least two months, and even more preferably at least six months.

The pharmaceutical composition is prepared by loading the chemokine into a polymer bonded to a sulfated glycosaminoglycan. The term "loading," as used herein, refers to contacting the polymer bonded to sulfated glycosaminoglycan with an amount of the chemokine such that a sufficient amount of the chemokine will become associated with the sulfated glycosaminoglycan. The chemokine associates with the sulfated glycosaminoglycans as a result of the affinity of the chemokine for the sulfated glycosaminoglycan. A sufficient amount of the chemokine is an amount that will provide a therapeutically effective dose of the chemokine as the chemokine is released from the pharmaceutical composition after being contacted with the subject.

The polymer used in the pharmaceutical composition can be any suitable biocompatible polymer. In some embodiments, the polymer is a biodegradable polymer, while in other embodiments the polymer is a non-biodegradable polymer. Examples of suitable biocompatible polymers may include, but are not limited to, polyalkylene oxides, polymethacrylates, polyurethanes, cellulosics, polyhydroxyalkyl acrylates, polyesters, and the like, and combinations of two or more thereof. In some embodiments, the polymer is a gel, e.g., a hydrogel. Other examples of biocompatible polymers may include, but are not limited to, polymers comprised of at least one polyethylene monomer, such as polyethylene glycol (PEG) or polyethylene oxide, polymers comprised of polyamine monomers, such as polyethyleneimine (PEI), polylysine, and poly(L-lactide) (PLLA), poly-p-dioxanone (PDO), polycaprolactone (PCL), polyvinyl alcohol (PVA), poly(lactide-co-glycolide) (PLG), and the like, and combinations of two or more thereof.

In some embodiments, the polymer can include or be formed from a natural polymer such as a protein. The protein can be linked to any of the polymers described herein, or it can be used as the polymer itself. Preferably the protein includes suitable reactive sites such as amine groups that facilitate bonding to the sulfated glycosaminoglycan. For example, the polymer may be formed from serum albumin proteins, such as human serum albumin, bovine serum albumin, or rat serum albumin. Inclusion of an albumin in the polymer provides at least two advantages. First, albumin is very biocompatible. Second, the albumin includes free amine groups that can be used as a linkage site for attachment of glycosaminoglycans, which bear carboxylate groups, using, for example, carbodiimide chemistry.

The polymer is bonded to the sulfated glycosaminoglycan to provide a pharmaceutical composition that can be loaded with a chemokine. Preferably, the polymer is bonded to the sulfated glycosaminoglycan by crosslinking of the polymer with the sulfated glycosaminoglycan. Examples of possible crosslinker chemistry include, but are not limited to, isocyanate chemistry, carbodiimide chemistry, succinimide chemistry, maleimide chemistry, and any other crosslinking chemistry known in the art. The chemistry used to bond or crosslink the polymer to the sulfated glycosaminoglycan should be chosen to make use of reactive groups present on the polymer and the sulfated glycosaminoglycan. For example, carbodiimide chemistry is suitable for bonding or crosslinking the amino function of albumin or a suitable polyamine with the carboxyl groups present on sulfated glycosaminoglycans. Combination of the polymer with the sulfated glycosaminoglycan provides a material that both has an affinity for chemokines, while also preventing the glycosaminoglycans from being water soluble.

A number of different types of sulfated glycosaminoglycans are known to those skilled in the art. For example, in some embodiments, the sulfated glycosaminoglycans are selected from the group consisting of heparin, chondroitin sulfate A, and chondroitin sulfate B. Sulfated glycosaminoglycans having an affinity for the desired chemokine should be selected. Affinity of the sulfated glycosaminoglycan for the chemokine can be determined using an assay. For example, the affinity of sulfated glycoaminoglycan for the chemokine can be determined using surface Plasmon resonance or by using release experiments. Generally, only a single type of sulfated glycosaminoglycan having an affinity for a particular chemokine is used. However, in other embodiments, the polymer is crosslinked with a plurality of different types of sulfated glycosaminoglycans. This can be used either to provide the delivery of multiple chemokines, or to provide for a more complex release profile based on the differing affinities of the different types of sulfated glycosaminoglycans present.

The pharmaceutical composition can have a variety of characteristics, depending on the desired application for the composition and the polymer and bonding chemistry chosen for preparation of the composition. For example, in some embodiments, the pharmaceutical composition can be an injectable composition, such as a gel (e.g., a hydrogel). Another injectable form of the pharmaceutical composition is microparticles. In other embodiments, the polymer has a more rigid structure, such as what one would find in a preformed device. Examples of preformed devices range in size from matchstick-sized cylindrical rods such as the Norplant™ (levonorgestrel) and Zoladex™ (goserelin acetate) implants, microspheres such as are sold under the trade name Lupron Depot™ (leuprolide acetate). The shape of the preformed device can be designed to better fit within a cavity in the body. For example, in some embodiments, the preformed device can be configured for transvaginal placement. For example, the preformed device can be a polymeric ring suitable for vaginal placement. Suitable implants are also available for treating male urinary stress incontinence. See for example U.S. Pat. No. 7,896,798, the disclosure of which is incorporated herein by reference.

Another aspect of the invention provides a method for providing sustained release of a chemokine to subject, comprising contacting the subject with a pharmaceutical composition including a polymer bonded to a sulfated glycosaminoglycan and loaded with a chemokine having affinity for the sulfated glycosaminoglycan. As used herein the term contacting refers to bringing about direct contact between the pharmaceutical composition and the tissue and/or biological fluids of the subject such that they are in immediate proximity or association with each other. Contacting can occur, for example, as a result of administration or implantation of the pharmaceutical composition. A subject, as defined herein, is an animal, preferably a mammal such as a domesticated farm animal (e.g., cow, horse, pig) or a pet (e.g., dog, cat). More preferably, the subject is a human. In some embodiments, the subjects can have a specific gender; i.e., male or female. The subject may also be a subject in need of treatment for a disease, such as a sexually transmitted disease, or an injury, such as that which occurs in stress urinary incontinence Sustained chemokine release can be used to treat any disease in which chemokines play an important role. See for example, a review of chemokines and disease (Bendall, L., Histol Histopathol., 20, 907-926 (2005)), the disclosure of which is incorporated herein by reference. Examples of diseases suitable for treatment by the pharmaceutical composition of the present invention include cardiovascular disease, arthritis, multiple sclerosis, asthma, graft rejection, atherosclerosis, cancer, injury (e.g., stress urinary incontinence), and sexually transmitted disease (e.g., HIV-associated disease).

Another aspect of the invention provides a method for treating or preventing infection of a subject by a sexually transmitted disease. The method includes contacting the subject with a pharmaceutical composition including a polymer bonded to a sulfated glycosaminoglycan and loaded with a chemokine having affinity for the sulfated glycosaminoglycan, wherein the chemokine is effective for treating the sexually transmitted disease, and a therapeutically effective amount of the chemokine is released to the subject. Examples of sexually transmitted diseases include Chlamydia, Herpes, Gonorrhea, infection by Human Papillomavirus, Syphilis, Trichomoniasis, and infection by human immunodeficiency virus (HIV). For example, in some embodiments, the sexually transmitted disease is human immunodeficiency virus, which is a lentivirus that causes the acquired immunodeficiency syndrome, and the chemokine is CCL5. In further embodiments, the subject is human, while in other embodiments the subject is male or female.

Another aspect of the invention provides method of treating a tissue injury in a subject in need thereof. Tissue injury includes injury to tissue, which includes epithelial, connective, nerve, and muscle tissue. Injury to the tissue can come from a variety of sources, such as disease, surgery, burns, laceration, or any other source of wounds. The method includes positioning a pharmaceutical composition including a polymer bonded to a sulfated glycosaminoglycan and loaded with a chemokine having affinity for the sulfated glycosaminoglycan proximal to the injury, wherein the chemokine of the pharmaceutical composition is effective for attracting mesenchymal stem cells to the injury. For example, in some embodiments the subject has been diagnosed as having stress urinary incontinence, and the chemokine is CCL7. Stress urinary incontinence, which can occur in both male and female subjects, is incontinence that is prompted by a physical movement or activity, such as coughing, sneezing, running or heavy lifting, which is used to diagnose stress urinary incontinence from other types of urinary incontinence, and can occur as a result of injury to the tissue of the urinary tract.

Another aspect of the invention provides a method for treating or preventing cardiovascular disease in a subject. The method includes contacting the subject with a pharmaceutical composition including a polymer bonded to a sulfated glycosaminoglycan and loaded with a chemokine having affinity for the sulfated glycosaminoglycan, wherein the chemokine is effective for treating or preventing the cardiovascular disease, and a therapeutically effective amount of the chemokine is released to the subject. For example, in some embodiments, the cardiovascular disease is myocardial infarction. In cardiovascular disease, it is beneficial to block neutrophil influx and recruitment of hematopoietic cells. Accordingly, in some embodiments of treating cardiovascular disease, the chemokines used can include CCL5 and CXCL12.

The present invention is illustrated by the following examples. It is to be understood that the particular examples, materials, amounts, and procedures are to be interpreted broadly in accordance with the scope and spirit of the invention as set forth herein.

EXAMPLES

Example 1: Using Glycosaminoglycan/Chemokine Interactions for the Long-Term Delivery of 5P12-RANTES in HIV Prevention With 2.6 million new infections per year, the spread of the Human Immunodeficiency Virus (HIV) is a global epidemic. One strategy to stop the spread of HIV is to develop ways to prevent person to person transmissions. Due to societal reasons, proven methods such as condom usage and circumcision are often not adopted. Application of topical agents to decrease HIV transmission when applied to the genital mucosa before intercourse is a strategy that has been shown to be plausible in non-human primate models and has shown utility in one large clinical study. Currently, the delivery of low molecular weight pharmaceutical HIV preventatives using vaginal gels has shown the most clinical progress. Results from a recent clinical trial delivering tenofovir using a gel based on hydroxyethylcellulose (HEC) have yielded especially encouraging results, as HIV acquisition was reduced by an estimated 39%. Abdool et al., Science 329 (5996), 1168-74 (2010). A major concern with the large scale use of reverse transcriptase inhibitors (RTIs) is that if these agents are simultaneous used in HIV therapy there is the potential for the development of resistant strains. Use of these therapeutics in undiagnosed HIV-positive women, could potentially promote the selection for resistant viruses. Of additional significance is the increasing prevalence of viruses resistant to classes of antiretrovirals widely used in a community. Thus application of antiretroviral agents for topical prevention of HIV-1 acquisition that have similar resistance patterns to agents used widely for therapy may limit the utility of these strategies. The development of agents that do not share resistance patterns with current antiretroviral therapeutics is therefore desirable as is the exploration of combination strategies for prevention of infection.

RANTES (CCL5) is a chemokine that binds to the chemokine receptor CCR5, which also serves as a co-receptor for HIV cellular entry. The binding of chemokine to CCR5 subsequently leads to internalization of the receptor, and as a result, prevents HIV binding and infection. Vangelista et al., Vaccine, 26(24), 3008-15 (2008); Lusso et al., Faseb J. 25(4), 1230-43 (2011). Within hours after RANTES exposure in vitro, however, receptor cycling occurs and unoccupied CCR5 is available on the cell surface again and susceptibility to infection returns. Hartley et al., Proc Natl Acad Sci USA 101(47), 16460-5 (2004). This receptor cycling is the most important reason for continued presence of RANTES in order to prevent HIV binding.

More potent RANTES analogs with more durable effects on CCR5 availability have been developed to try to address this problem. However, receptor cycling is only prolonged from few hours to few days by these analogs, indicating a need for sustained delivery over multiple days. Some of these analogues can also occupy CCR5 without inducing receptor internalization or signaling, thereby avoiding potential induction of cellular activation and inflammation. Gaertner et al., Proc Natl Acad Sci USA, 105, (46), 17706-11 (2008). While a single report suggests that low level resistance to PSC-RANTES could be found in a SHIV isolate found in a rhesus macaque that was not protected by a relatively low dose of analog before virus challenge, it has since been clearly demonstrated that evolution of resistance to both PSC-RANTES and 5P12-RANTES (a more recently developed analog) is disfavored by a high fitness cost. Nedellec et al., PLoS One, 6, (7), e22020 (2009). Both 5P12-RANTES and PSC-RANTES have provided complete protection against SHIV infection in the rhesus vaginal challenge model, but the challenge took place no more than 30 minutes after topical application of the analog. Veazey et al., J Infect Dis, 199, (10), 1525-7 (2009). Delivery methods that can provide sustained delivery of these agents would be desirable: strategies that provide durable protection against HIV acquisition are more likely to be effective than those heavily dependent upon timing of application relative to coitus. While sustained delivery of RANTES analogs has been explored in a microparticulate system, the long-term sustained dosage of 5P12-RANTES needed for HIV protection is still unclear. A sustained, long-term (weeks-months) delivery system where delivery can be modified is needed to further explore the use of RANTES analogs as a topical HIV prevention strategy.

In this study, the affinity strength of different GAGs to RANTES analogs (e.g., 5P12 RANTES) was characterized. Solid delivery implants were designed exploiting these different affinity strengths and examined release of RANTES analogs from materials made from these GAGs. It was also found that incorporating different amounts and types of GAGs into a sustained delivery system can determine the pace and magnitude of long-term drug delivery. These observations can be used for generating short term drug delivery gels similar to HEC gels, or long term drug delivery inserts similar to other HIV microbicide delivery inserts currently under investigation. This represents the first use of GAGs to prolong the delivery of either HIV microbicides or chemokines.

Materials and Methods

Heparin sodium, chondroitin sulfate A (CSA) and chondroitin sulfate B (CSB, also known as dermatan sulfate) were all purchased from Thermo Fisher Scientific (Pittsburgh, Pa.). 5P12-RANTES was provided by the Mintaka Foundation for Medical Research, Geneva, Switzerland). DUOSET™ Human ELISA kits were purchased from R&D Systems. Fluorochrome labeled monoclonal antibodies (3A9 APC, APC isotype, 2D7 FITC, FITC isotype, CD8 PE-Cy7, and CD3 PerCP) were all purchased from BD biosciences (Franklin Lakes, N.J.). Surface Plasmon Resonance (SPR) supplies were purchased from General Electric (GE Healthcare, Piscataway, N.J.). All other reagents used in this study were purchased from Thermo Fisher Scientific (Pittsburgh, Pa.) unless otherwise stated.

Surface Plasmon Resonance (SPR) Analysis

SPR was used to study the affinity between different GAGs and 5P12-RANTES using the Biacore 3000 system (GE Healthcare). A CM5 sensor chip (GE Healthcare) was used for all SPR experiments. The BIAEVALUATION™ software (version 4.0.1, GE Healthcare) was used for all post experiment analyses, including curve fitting and kinetic parameter determination. The optimum protein immobilization condition was determined to be pH 5.5 after pH scouting. Immobilization of 5P12-RANTES onto the chip was carried out by amine coupling. Specifically, the surface was activated by injecting 0.4M 1-ethyl-3-(3-dimethylpropyl)-carbodiimide (EDC)/0.1M N-hydroxysuccinimide (NHS), 5P12-RANTES (50 µg/ml in acetate buffer (pH 5.5)) in was then injected for the actual immobilization. Inactivation of excess groups was carried out by injection of 1M ethanolamine-HCl (pH 8.5). The specific rate and time of injection for each step was automated to reach the targeted immobilization level of 3000 response units (RU) units. After washing the surface with 10 mM HEPES buffer (pH 7.4), association and dissociation studies were carried out by injecting samples at 10 µl/min for 90 secs (association) and then washing the surface with acetate buffer (pH 4.5), also at 10 µl/min for 4.5 mins (dissociation). Heparin sodium, CSA and CSB samples at various concentrations (ranging from 0.25 µM to 20 µM) were examined for real-time affinity interaction with 5P12-RANTES. Dissociation constants were calculated by using the simultaneous kinetics ka/kd fit in the BIAEVALUATION™ software.

Polymer Synthesis and Washing

Hydrogels are networks of crosslinked hydrophilic polymers commonly used in drug delivery. The polymeric hydrogels used in this study were firm, solid disks synthesized by crosslinking bovine serum albumin (BSA) with different GAGs using carbodiimide chemistry. BSA was selected as a relatively inert base material of high natural bioavailability and with readily available amines for crosslinking chemistry. Separate mixtures totaling 100 mg of 50:50, 25:75, 15:85, 5:95 and 2.5:97.5 heparin to BSA, 25:75 CSA to BSA and 25:75 CSB to BSA ratios were weighed and individually dissolved in 500 µl of 0.1M 2-(N-morpholino) ethanesulfonic acid (MES) solution (pH adjusted to 5.2 using 0.1N NaOH). Separately, 40 µl solutions of 1 mg/ml of EDC in 0.1M MES were prepared. On ice, each 500 µl GAG/BSA solution was thoroughly mixed and vortexed with the 40 µl EDC crosslinker solution in a 15 mm scintillation vial. The solutions were left to reach room temperature and allowed to cure overnight to form the firm, solid disks. After 24 hrs, the disks were removed from the vials and washed 3 times. Each wash cycle consisted of swelling the disks in 10 ml of PBS and leaving them in gentle agitation for 1 hour. At the end of the 3 wash cycles, the disks were left in gentle agitation overnight before air drying in the hood.

Polymer Characterization—Fourier Transform Infrared Spectroscopy (FTIR)

To prepare the samples for FTIR, dried polymers were ground into powder using a mortar and pestle. The powdered polymers were washed in 5 ml of deionized (DI) water by vortex. The GAG/BSA powders were collected by centrifuging at 150 g. This wash cycle was repeated 3 times and the samples collected by freeze drying. FTIR of the freeze dried powder was performed along with unmodified BSA and GAGs to ensure that BSA and GAG was chemically conjugated, not just physically mixed or entangled. FTIR of the freeze dried powder was performed on the EXCALIBUR™ FTS 3000 Fourier-Transform Infrared (FTIR) Spectrophotometer (BioRad, Hercules, Calif., USA).

Gel Swelling

Polymer swelling was determined by incubating the dried polymer disks in pH 4.5 and pH 7.4 buffers overnight. Swelling ratio was calculated using the formula below.

$$\text{Swelling} = \frac{(\text{Swollen Weight} - \text{Dry Weight})}{\text{Dry Weight}} \times 100\%$$

Preparation of Simulated Vaginal Fluid (SVF)

To mimic release in a vaginal vault, release occurred in SVF, which was prepared by a slight modification of a published formula. Aka-Any-Grah et al., Eur J Pharm Biopharm, 76, (2), 296-303 (2010). To 900 mL of distilled water, NaCl (3.51 g), KOH (1.4 g), Ca(OH)$_2$ (0.22 g), bovine serum albumin (10 g), lactic acid (2.00 g), acetic acid (1.00 g), glycerol (0.16 g), urea (0.4 g) and glucose (5.00 g) were added and stirred mechanically until complete dissolution. More BSA was added than in the published formula to counter adsorption of protein to glass. In addition to being used in crosslinked form as a polymeric hydrogel material in this study, BSA is a typical stabilizing protein used in many release studies to prevent protein loss due to adsorption onto glass- or plastic ware. The pH of the mixture was then adjusted to 4.5 using HCl, and the volume was adjusted to 1 L. The SVF was filtered using a 0.2 µm pore filter before used in the release study.

Drug Loading of Polymers

5P12-RANTES was loaded into the GAG/BSA polymers by hydrodynamic loading. The 5P12-RANTES loading solution was prepared by dissolving freeze-dried 5P12-RANTES in SVF to reach a final concentration of 500 µg/ml. Each dried gel was incubated in 250 µl of 5P12-RANTES solution in wells of a 24 well plate (1.5 cm diameter). The wells were sufficiently large to accommodate the size of the fully swollen gel. The disks were allowed to swell for 48 hrs to allow the disks to fully load. The fully loaded disks were weighed before the start of the release study.

In Vitro Drug Release

5P12-RANTES release profiles from the GAG/BSA polymers were characterized by an in vitro release study. The release study was carried out by incubating each loaded gel (wet) into 1 mL of SVF solution in a 1.5 cm diameter well. The disks were incubated at 37° C. under gentle agitation using a incubator shaker (LAB-LINE™ incubator-shaker model 3525). At each time point, each gel was carefully removed from its release solution using tweezers and was subsequently placed into a new well containing fresh SVF. The aliquots containing released 5P12-RANTES were then aspirated and stored in 400 ul aliquots at −20° C. for later analysis. Daily samples were taken for the first 10 days, followed by sampling every other day for 4 weeks. Levels of 5P12-RANTES in each aliquot were measured by RANTES ELISA. Daily and cumulative release profiles were plotted against time.

Characterization of the Authenticity of Receptor Binding by Released 5P12-RANTES While the human ELISA kit was used to quantify 5P12-RANTES in the release aliquots, a human T-Cell receptor binding bioassay was used to confirm authentic receptor binding of the released 5P12-RANTES. This was done by comparing detection levels of the 3A9 and 2D7 epitopes of CCR5 in the presence of the 5P12-RANTES samples. The murine monoclonal antibody 2D7 specifically targets the second loop of CCR5, while another, 3A9, targets the receptor's amino-terminal loop. Binding of RANTES to CCR5 has been shown to block antibody binding to the second loop, but not to the amino-terminal one. After provision of written informed consent through a protocol approved by the institutional review board (IRB) of University Hospitals of Cleveland/Case Medical Center, peripheral blood mononuclear cells (PBMC) were prepared by FICOLL-PAQUE™ density sedimentation from the blood of healthy adult volunteers. PBMCs (2×10$^6$ cells/well in 24 well plates) were incubated in medium (RPMI supplemented with 10% FBS, L-glutamine and antibiotics) with or without aliquots containing previously released 5P12-RANTES. As a positive control, fresh stock solutions of 5P12-RANTES were used to establish standard bioassay values. After 1 hr of incubation, cells stained with fluorochrome-conjugated antibodies that recognize CD3, CD8 and CCR5 (3A9 and 2D7) for 15 minutes on ice prior to analysis on a BD LSRII flow cytometer (BD, Franklin Lakes, N.J.).

Results

Surface Plasmon Resonance (SPR) Analysis

The SPR analysis of heparin/5P12-RANTES interaction measures the real-time interaction between immobilized 5P12-RANTES and free heparin (or other GAGs) in solution. The analysis consists of a set of sensorgrams obtained by measuring the refractive indices on the chip surface as GAG solutions of different concentrations flow over a 5P12-RANTES immobilized chip. The refractive index changes (represented as response units (RU)) as GAG molecules bind (specifically or non-specifically) to the chip surface. An increase in RU units generally reflects increased binding interaction (specific or non-specific) between the immobilized molecule (5P12-RANTES) on the chip and the analyte (GAG) in solution flowing above the chip.

SPR Analysis of GAG Interactions with 5P12-RANTES

The sensorgrams (FIG. 1) from the GAGs/5P12-RANTES SPR study showed heparin had the fastest association (sharpest increase in RU after injection of GAG), and the slowest dissociation (slowest decrease in RU relative to max RU). CSB showed slower association and faster dissociation compared to the heparin. CSA, however, showed almost no interaction as the RU level returned to baseline almost immediately after wash.

SPR Analysis of GAG-5P12-RANTES Affinity with Concentration Sensorgrams

In general, all the sensorgrams (FIG. 2) in the heparin concentration study showed similarly shaped characteristic profiles. The association step consists of a rapid initial response followed by a slower gradual increase and the dissociation (wash) step showed an immediate rapid drop in response followed by gradual decrease over time. Closer examination of the association and dissociation phases of the sensorgrams does show minor differences in both association and dissociation phases with varying concentration. This may reflect multiple interactions possible with higher heparin concentrations, leading to a slight overestimation of Kd at higher concentrations, however its effect appears to be minor.

The results from the SPR analysis of the CSB/5P12-RANTES interactions with different CSB concentrations (FIG. 3) confirmed the initial findings that CSB had weaker affinities to 5P12-RANTES when compared with heparin. As was found with heparin, all the sensorgrams in the CSB/5P12-RANTES study showed a very rapid initial response followed by a more gradual increase in the association phase, and a short rapid drop in response followed by very gradual decrease over a long time. One difference is that the CSB/5P12-RANTES study did not exhibit the saturation effect observed in the heparin study. During the dissociation phase, drops in response level corresponded with all CSB concentrations tested.

Using the BIAEVALUATION™ software, simultaneous 1:1 ka/kd fit was performed on the four unsaturated heparin concentrations and the calculated dissociation constant (Kd) was 25.5 nM. This result is similar to the published Kd (32.1 nM) of unmodified RANTES with heparin. Martin et al., Biochemistry, 40, (21), 6303-18 (2001). A similar SPR concentration study of CSB/5P12-RANTES interactions was performed and the calculated Kd was 1.07 mM.

Polymer Formation and Characterization

The 50:50 heparin:BSA mixture did not form materials that stayed intact after drying and swelling, thus it was not analyzed further in these studies. All of the remaining mixtures (25:75, 15:85, 5:95 and 2.5:97.5 heparin to BSA, 25:75 CSA to BSA and 25:75 CSB to BSA ratios) formed materials that stayed intact after removal from the vial, 24 hrs following synthesis.

FTIR of Heparin/BSA Polymers

The conjugated heparin/BSA spectra (FIG. 4) contained a combination of characteristic peaks of unmodified BSA (amide I and II bands from the amide backbone) and characteristic peaks of unmodified heparin (symmetrical and asymmetrical stretching of S—O from the $SO_3$ groups in heparin). In addition, however, conjugated heparin/BSA showed a small decrease in OH-stretching and in OH-bending when compared with just a physical mixture of heparin and BSA.

Hydrogel Swelling

Hydrogel swelling (Table I) in pH 7.4 buffer for all materials tested (BSA only, 25% heparin and 25% CSB) was not significantly different, regardless of the type of GAG used. However, when swelling was performed in a slightly acidic environment (pH 4.5), swelling was significantly decreased for gel systems containing relatively large CSB (25%) and heparin (25%, 15%) content, whereas swelling for BSA only, CSA (25%) and materials with lesser heparin content (5% and 2.5%) all remained relatively high.

TABLE I

Hydrogel swelling of GAG/BSA hydrogels in pH 4.5 and pH 7.4 buffers.

| | BSA only | 25% CSA | 25% CSB | 25% hep | 15% hep | 5% hep | 2.5% hep |
|---|---|---|---|---|---|---|---|
| Swelling (%) pH 4.5 | 333 ± 4 | 344 ± 12 | 147 ± 4 | 133 ± 16 | 131 ± 9 | 269 ± 4 | 306 ± 6 |
| Swelling (%) pH 7.4 | 275 ± 11 | | 285 ± 6 | 278 ± 11 | | | |

In Vitro 5P12-RANTES Release from GAG/BSA Gels

The 5P12-RANTES release in all GAG/BSA polymers appeared to consist of two phases—a burst phase over the first few days in which relatively large amounts of 5P12-RANTES are released and a slower release phase thereafter. The amount and type of GAG content within the polymers had a significant impact on both phases and these effects were explored in more detail in two different studies. Results from each release study are presented both as release at each time point when the disks were moved to fresh SVF solution and cumulative release, normalized to essentially 100% total release by day 33 (by which time daily release had become negligible). This calculation is less accurate for affinity-based systems as they still were releasing approximately 50,000 pg/day by day 33, however this represents only a small fraction of the 1 to 10 million pg released in early time points. One can therefore conclude that this 100% estimate is sufficient, and any error would represent even more constant, sustained release.

Effect of Different GAG Types on Release

Figure 5:
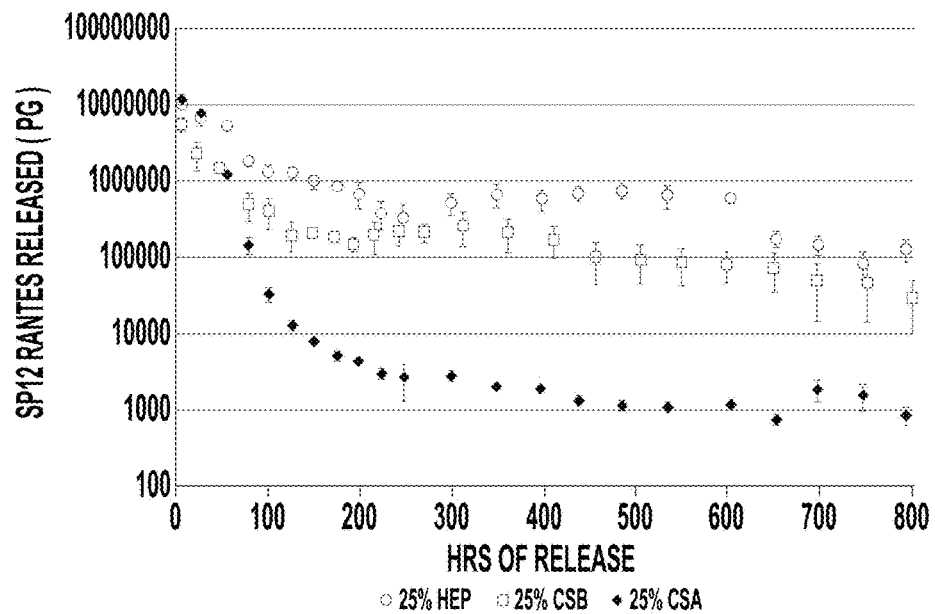
FIG. 5 is a graph showing 5P12-RANTES released at each time point from polymers containing different GAGs. Heparin/BSA (○) disks showed the highest level of sustained release. CSB/BSA (■) disks also showed substantial and sustained levels of release. CSA/BSA (♦) disks resulted in release profiles with the lowest sustained release, similar to the release in BSA-only control disks (not shown). Error bars represent standard deviation of means.
Figure 6:
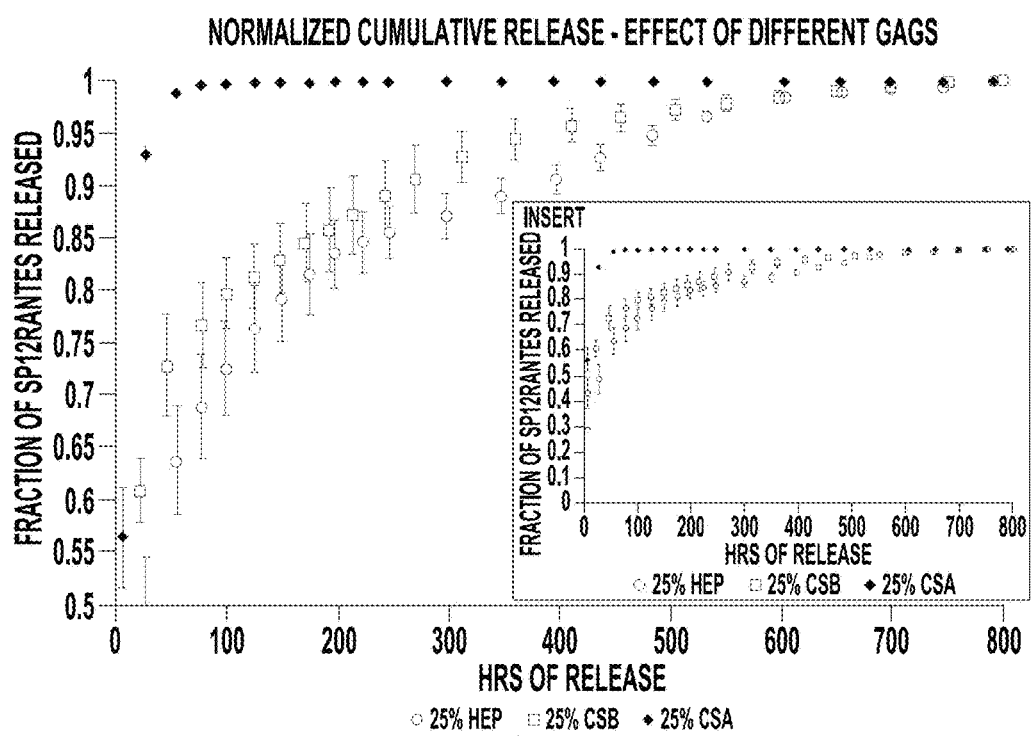
FIG. 6 provides a graph showing the normalized cumulative release profile from GAG/BSA polymers. The Heparin/BSA (○) disks resulted in the most sustained release, followed by CSB/BSA (■) disks. The CSA/BSA (♦) disks resulted in the least sustained release. Error bars represent standard deviation of means. The main graph and the insert presented in the figure represent the same data. The main graph is zoomed in to highlight the sustained release.

The release profiles from the different GAG/BSA polymers (FIGS. 5 & 6) reflected the affinity strength of GAG/5P12-RANTES within the gel. Gels containing GAGs with stronger affinity to 5P12-RANTES generally resulted in more sustained release profiles. In detail, in the burst phase, release from the CSA/BSA disks resulted in a drop by four orders of magnitude in the amount of 5P12-RANTES released when comparing the first day of release to the fifth day of release. In heparin/BSA and CSB/BSA disks, this burst effect was reduced: a drop of only 1.5 orders of magnitude was observed. After 5-7 days, the release profiles of the latter two materials appear to transition into a more constant release phase. This phase consisted of more constant levels of 5P12-RANTES released from the polymer systems, although the levels of 5P12-RANTES released decreases with time, but at a much slower rate than during the initial burst phase. In this more constant release phase, the release level seems related to GAG/5P12-RANTES affinity strength within the polymer disks. The heparin/BSA disks (highest affinity) exhibited higher proportions of sustained release compared to the disks with lesser affinity (CSB/BSA followed by CSA/BSA).

Effect of Heparin Content on 5P12-RANTES Release

Figure 7:
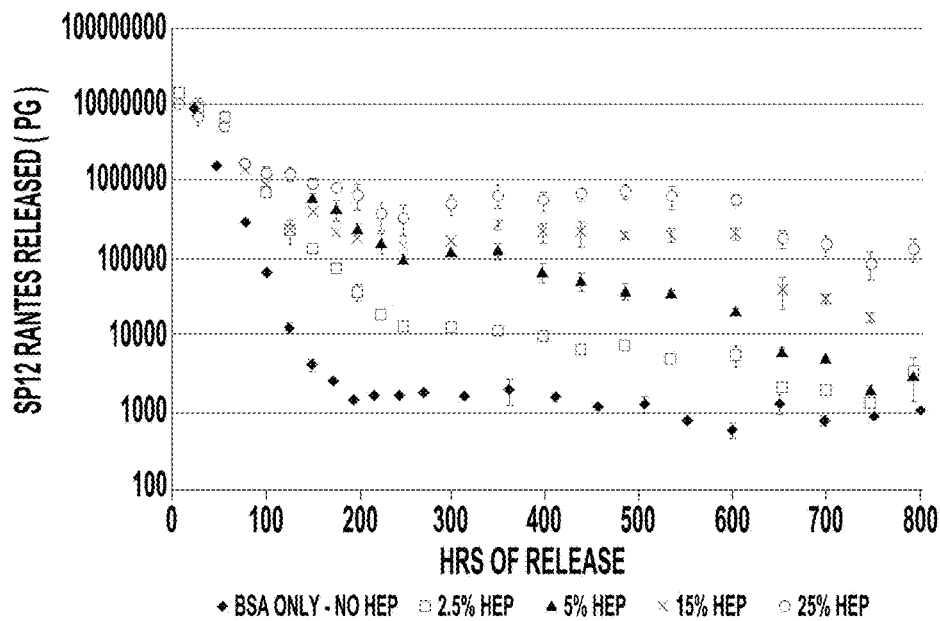
FIG. 7 is a graph showing 5P12-RANTES release from polymers containing incremental heparin fractions—BSA only (no heparin) (♦), 2.5% heparin (■), 5% heparin (▲), 15% heparin (x) and 25% heparin (●). All the release curves are characterized by an initial burst phase, and then followed by a sustained release. In the burst phase, an increase in heparin content appears to decrease the burst effect, whereas in the sustained release, increases in heparin content corresponded with increases in release at each time point. Error bars represent standard deviation of means.
Figure 8:
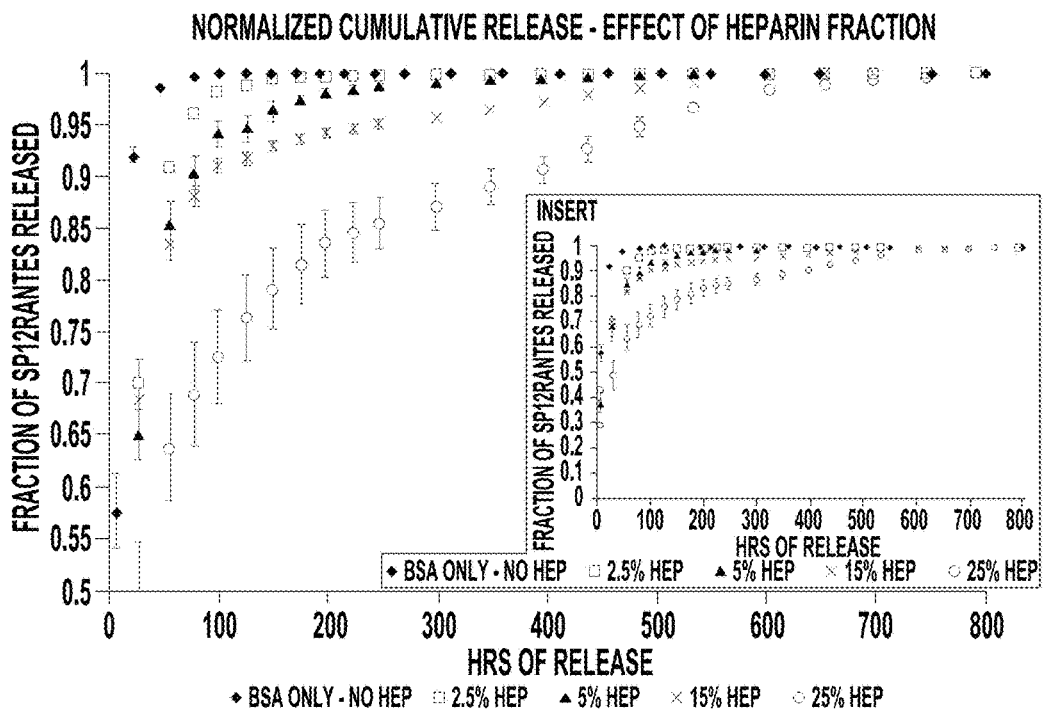
FIG. 8 is a graph showing the normalized cumulative release profiles from heparin/BSA polymers. Gels tested include: BSA only (no heparin) (♦), 2.5% heparin (■), 5% heparin (▲), 15% heparin (x) and 25% heparin (●). The main graph and the insert presented in the figure represent the same data. The main graph is zoomed in to highlight the sustained release. Sustained release from the heparin/BSA disks corresponded with heparin content, more sustained release profiles were observed for polymers with higher heparin content. Error bars represent standard deviation of means.

The release profiles from the polymers with different heparin (FIGS. 7 & 8) content showed a relationship between heparin content and release profile, with disks containing more heparin generally resulting in more sustained release profiles. In the burst phase, release from the BSA-only disks resulted in a drop by four orders of magnitude in the amount of 5P12-RANTES released when comparing the first day of release to the fifth day of release. In disks containing conjugated heparin, this burst effect was reduced as the heparin content increased. This reduced burst effect was due to a combination of both decreased 5P12-RANTES release initially and higher 5P12-RANTES release at the end of the burst phase. In the case of disks containing 25% heparin, comparing the first day and fifth day of release, a drop of only 1.5 orders of magnitude was observed. After 5-7 days, the release profiles appear to transition into a more constant release phase. In this phase, the release dose seems to relate to the amount of covalent heparin within the polymer disk. The disks with higher heparin content exhibited higher levels of 5P12-2RANTES release compared to the release from disks with lesser heparin conjugation or the no heparin control.

CCR5 Blocking Assay

In preliminary studies, it was confirmed that 5P12-RANTES blocks the binding of monoclonal antibody 2D7 to the second extracellular loop of CCR5 while binding of 3A9 is mostly unaffected by 5P12-RANTES binding to CCR5.

CD8$^+$ T-cells were analyzed in a receptor blocking assay. The 2D7% presentation and 3A9% presentation were analyzed to determine CCR5 receptor blocking efficacy of 5P12-RANTES which had been incorporated and released from the delivery system. Successful 5P12-RANTES blocking of the CCR5 receptor is expected to result in a decrease in 2D7% presentation while not affecting levels of 3A9% presentation. Binding of 5P12-RANTES to the CCR5 receptor occupies the 2D7 antibody binding site, thus decreasing the level of 2D7% presentation detected by the antibody. Conversely, 5P12-RANTES binding does not occupy the 3A9 antibody binding site, thus the levels of 3A9% presentation is largely unaffected by 5P12-RANTES occupancy of CCR5 receptors.

Figure 9:
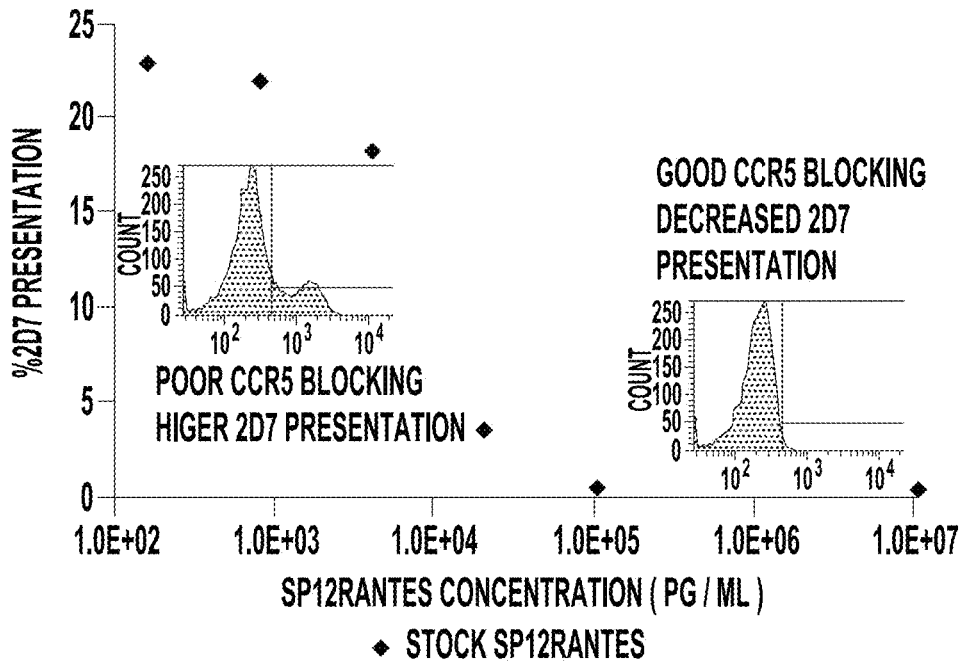
FIG. 9 is a graph showing the CCR5 blocking capacity of stock 5P12-RANTES as determined by monoclonal antibody (clone 2D7) binding. In samples where 5P12-RANTES concentrations were greater than 100 ng/ml, 2D7% presentation was less than 1%, indicating good CCR5 blocking. In samples where 5P12-RANTES concentrations were below 0.8 ng/ml, 2D7% presentation was at or greater than 20%, suggesting little to no CCR5 blocking (this level is similar to that of no 5P12-RANTES, the negative control). Insets show FACS histograms of 2D7 presentation on the studied PBMCs at low and high 5P12-RANTES concentrations.

The 5P12-RANTES CCR5 blocking efficiency of 5P12-RANTES at different stock concentrations dissolved in SVF was studied and plotted in FIG. 9. At stock 5P12-RANTES concentrations of 100 ng/ml or greater, the blocking assay showed good CCR5 blocking as demonstrated by 2D7% binding (FIG. 9) of less than 1%; and 3A9% binding near 20%. At concentrations of 0.8 ng/ml or less, the blocking assay showed little to no CCR5 blocking with 2D7% binding (FIG. 9) and 3A9% binding (data not shown) both near 20%. These results were used to strategically dilute the released aliquots for the bioactivity assay.

Figure 10:
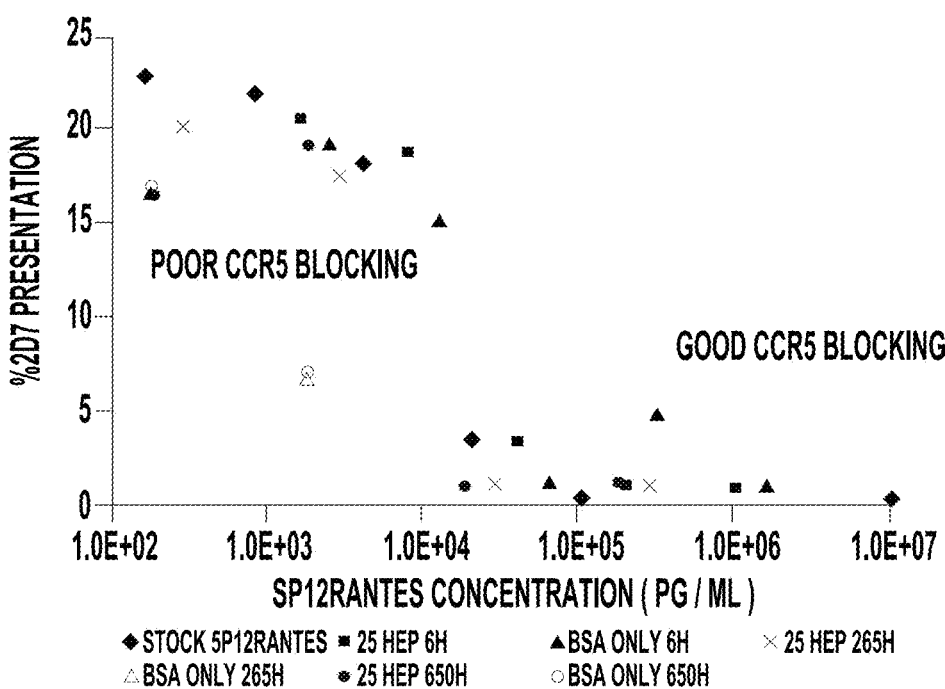
FIG. 10 is a graph showing the CCR5 blocking activity of the released aliquots from GAG/BSA polymers. Release aliquots from BSA and 25% heparin disks at 3 time points (6 h, 265 h and 650 h) were evaluated. Protein concentration were previously determined using ELISA, and samples were diluted to concentrations both one order of magnitude above and below the CCR5 blocking threshold. Each symbol represents that release sample at all of its tested dilution concentrations. Release samples at or above the blocking threshold concentration showed good blocking, while samples diluted to below the blocking threshold concentration showed poor blocking, comparable to that of stock 5P12-RANTES.

Based on this capacity to detect CCR5 blocking with a competitive antibody binding assay, the blocking efficiency of select released aliquots was examined to determine whether incorporated and released drug maintained its bioactivity following incorporation, long-term aqueous incubation, and drug release. Samples from three release time points (6 h, 265 h and 650 h) were examined. Each released aliquot was strategically diluted based on its measured concentration (from ELISA) such that one dilution was at a concentration expected to result in good CCR5 blocking, a second dilution would be expected to result in a concentration with little CCR5 blocking and a third dilution would be expected to result in a concentration with little to no blocking (based on stock 5P12-RANTES blocking results from FIG. 9). The CCR5 receptor blocking efficiency of samples released from the BSA disks and the 25% heparin disks are presented (FIG. 10) The results from the blocking assay corresponded with the expected activity of each sample based on its 5P12-RANTES concentration previously determined by ELISA. This indicates that blocking ability of the delivered drug was not lost, even after as much as 650 hours of aqueous incubation of the loaded drug delivery device. As an example, one 6 h release aliquot from the 25% heparin gel with a measured concentration of 10 µg/ml was diluted 250, 1250 and 6250 times, resulting in samples with expected concentrations of 40 ng/ml, 8 ng/ml and 1.6 ng/ml respectively. The blocking efficiency of these diluted samples was comparable to the blocking activity of stock 5P12-RANTES samples. More specifically 250× diluted release sample (expected concentration of 40 ng/ml) showed good blocking; the 1250× diluted sample expected concentration of 8 ng/ml) showing some blocking; and the 6250× diluted sample (expected concentration of 1.6 ng/ml) showing little or no CCR5 blocking. The CCR5 blocking assay was also performed for select release aliquots of the 25% CSA disks, 15% heparin, 5% heparin and 2.5% heparin disks. Release samples from all tested polymers showed the expected levels of blocking.

Discussion

SPR Analysis of GAG Interactions with 5P12-RANTES

Based on the relative rate of association and dissociation (the shape of the sensorgrams during the association and dissociation phases) and the dissociation constants obtained from the simultaneous ka/kd curve fitting (BIAevaluation software) of concentration sensorgrams, heparin appeared to have the strongest affinity for 5P12-RANTES, followed by CSB, then CSA. This ranking was consistent with published results from another study where interaction between unmodified RANTES and GAGs were examined (Martin et al., Biochemistry, 40, (21), 6303-18 (2001)), and corresponds to the relative number of sulfated groups per repeat unit (3, 2 and 1 for heparin, CSB and CSA respectively).

SPR Analysis of 5P12-RANTES to Varying Heparin Concentration

The shapes of the sensorgrams from the heparin/5P12-RANTES concentration study appear to be due to a combined effect of specific non-covalent heparin/5P12-RANTES binding and non-specific interactions. The RU response at the end of the association phase was related to the heparin concentration as increasing concentrations provided more heparin to interact (specifically and non-specifically) with the immobilized 5P12-RANTES. During the buffer wash (the dissociation step), the initial rapid drop is likely due to loss of heparin non-specifically interacting with the chip surface, while the subsequent gradual decrease in RU over a long time is likely due to dissociation of heparin bound to 5P12-RANTES on the chip surface. At a concentration of 2.5 µM (and higher), saturation is reached and no additional heparin can have specific interactions with the immobilized 5P12-RANTES on the chip surface. As a result, all additional increases in response at higher heparin concentrations at the end of the association phase were due to non-specific interactions. The non-specifically bound heparin molecules do not have strong binding and were quickly washed away at the beginning of the dissociation phase. After those heparin molecules were washed away, similar amounts of specifically bound heparin remain on the surface; thus, the subsequent response (in the gradual dissociation phase) for the more concentrated heparin solutions (2.5 µM or above) were almost identical. For more dilute heparin concentrations (1.0 µM or less), since saturation was not reached, the amount of specifically bound heparin is less than that of the higher concentration solutions; thus, responses are at lower RU levels and correlate with the initial solution concentration.

Polymer Characterization

FTIR of Heparin/BSA Polymers

The FTIR spectrum of the washed and ground up conjugated heparin/BSA materials confirms successful conjugation between BSA and heparin. Since BSA and heparin are both water soluble, the repeated washing of the conjugated heparin/BSA should have removed any free unconjugated BSA or heparin molecules from the crosslinked polymer. The FTIR spectrum of the heparin/BSA powder was a combination of characteristic peaks observed in neat BSA and neat heparin, indicating presence of BSA and heparin in the newly conjugated molecule. In addition, conjugated BSA-heparin also showed a slight decrease in OH bending and stretching when compared to a scan of physically mixed BSA and heparin. While the observed decrease is possibly within the range of detection, this would be how a reduction in the number of carboxylic acid groups, as they are being consumed in the conjugation reaction, would be manifested. Similar analysis was performed on CSA/BSA and CSB/BSA materials to confirm successful conjugation.

Polymer Swelling

The largest difference in swelling at different pHs was observed in polymers with highest heparin and CSB content. One possible explanation for this difference in swelling is that highly sulfated GAGs (heparin and CSB) in neutral pH (7.4) are negatively charged. The electrostatic repulsion between negative charges prevents the heparin molecules from close stacking, resulting in materials with relatively high swelling. However, in slightly acidic environments (pH 4.5), many of the carboxylic acid (unreacted) groups (pKa, typically around 5) are protonated, losing their negative charges and minimizing electrostatic repulsion. This observation has been extensively exploited in enteric drug delivery with polymeric hydrogels that swell with pH change. The decreased repulsion from fewer negative groups conceivable allows the molecules to be closer, leading to decreased swelling. In materials with relatively lower heparin content, this effect is somewhat minimized as there are not as many heparin molecules available to stack, resulting in still relatively higher swelling. Additional experiments like computational methods to model charge density distributions within GAGs would verify the mechanism of the noted difference in swelling.

In Vitro Release of 5P12-RANTES from GAG/BSA Polymers

Effect of Different GAGs on Release

The release profiles from the different GAG/BSA polymers showed a relationship between GAG affinity to 5P12-RANTES and the release profile, with polymers containing GAGs with stronger affinity to 5P12-RANTES resulting in more sustained release profiles. Specifically, from the SPR results, CSA showed the lowest affinity to 5P12-RANTES. Correspondingly, the CSA/BSA polymers showed the most significant burst effect and the least sustained release profile. CSB, with greater affinity to 5P12-RANTES than CSA, resulted in a release profile with a lesser burst effect, and a more prolonged and sustained release profile. Finally, disks containing heparin, the molecule with the greatest affinity to 5P12-RANTES had a smaller burst effect and the highest and most sustained prolonged 5P12-RANTES release. These results suggest that the affinity between GAG and 5P12-RANTES can be used to control release by decreasing the burst effect and sustaining release, thus creating a more sustained release profile.

Effect of Heparin Content on 5P12-RANTES Release

The differences in the release profiles of the disks can be attributed to the affinity between the 5P12-RANTES and the heparin within the gel. Initially, during the burst phase, in the BSA-only (no heparin) control disks, 5P12-RANTES diffuses down the concentration gradient and out of the polymers. There are no other mechanisms to slow this diffusion. After most of the 5P12-RANTES has diffused out of these disks, the gel transitions into a more constant release phase, where minimal release is observed and is likely due to some nonspecific interactions between BSA and 5P12-RANTES. In the disks with conjugated heparin, the affinity between the gel and the 5P12-RANTES retains some 5P12-RANTES within the delivery system in the beginning. The initial burst release of 5P12-RANTES from these disks is likely due to the diffusion of unbound 5P12-RANTES out of these polymers. After a few days, most of the 5P12-RANTES that remains within the polymer is bound to the polymer by reversible affinity interactions. The release during this phase is governed by the repeated association and dissociation of 5P12-RANTES to heparin within the polymer. This results in a more constant release. The heparin content incorporated into the polymers seems to determine the 5P12-RANTES released in this phase. The disks that contain more heparin have higher levels of this more constant release than do disks with lesser heparin content.

Blocking Assay

These data indicate that the 5P12-RANTES released from the GAG/BSA delivery systems maintain good biologic activity even after 4 weeks in the gel. The blocking activity of the released aliquots correlated well with the measured 5P12-RANTES concentrations in the aliquots (from ELISA). These results show that this delivery system does not interfere with the activity of the loaded 5P12-RANTES. This also supports the earlier observation that 5P12-

RANTES is stable in biological environments, and may even represent further stability bestowed by being incorporated in the drug delivery device.

CONCLUSIONS

In summary, the inventors have demonstrated GAGs can be strategically incorporated into a sustained delivery device for the long-term delivery of 5P12-RANTES. They have demonstrated the strength of affinity interaction can be used to modify long-term release profiles from these systems. Finally, they have shown our delivery system does not negatively affect the CCR5-binding activity of 5P12-RANTES. Moving forward, the method of gel formulation allows the delivery device to be made into any desirable shape (such as rings) by crosslinking the gel in a desired shaped mold. Thus, these disks, as currently constituted are ready to be used to study the feasibility of 5P12-RANTES as a long-term HIV preventative in an animal model. Beyond this immediate application, the use of BSA as a base inert material may raise some concerns. Human serum albumin has however been used in many biomedical applications (e.g., coating of medical devices). The observation that the type and amount of GAG can be used to modify long-term release profiles, and prove useful in other settings.

Example 2: Local Release of CCL7 from Affinity-Polymers Increases Retention of hMSC Around Urethra in Rats With an aging population in the US, the incidence of urinary incontinence is on the rise. A specific subset of urinary incontinence, resulting from tissue damage (such as from childbirth) is called stress urinary incontinence (SUI). Many of the incidences of post-partum SUI will resolve themselves on the order of months. However in the long-term it is estimated that nearly 40% of women will eventually suffer from chronic SUI in their lifetime. Treatment options for SUI include pelvic floor muscle training, electrical stimulation, injectable bulking agents, and surgical implantation of urethral slings. Of the patients requiring surgery, nearly 20% will require subsequent intervention. Within three years of surgery many patients continue to experience some level of incontinence. Additionally the urethral sling/mesh market has recently had some highly visible product recalls, following serious patient complications.

A new, cellular-based approach for regenerative repair of genitourinary tissue involves the injection of mesenchymal stem cells (MSCs), either systemically or locally, and has shown early promise in animal models of SUI. Kim et al., Urol. Int. 86 110-116 (2011). Despite the success of early MSC treatment in SUI, outcomes are inconsistent, and evidence shows cell migration away from the therapeutic site. C.-S. Lin, T. F. Lue, Stem Cells Dev. 21 834-843 (2012).

One of the challenges with MSC therapy is homing and retention of injected MSC to the site of injury. In SUI homing and retention of MSC depends on the presence of chemoattractant gradients in the vicinity of the urethra. Cruz et al., Obstetrics and Gynecology International. 2012 1-7 (2012). However, the duration of natural production of these chemokines is short (on the order of days). Since the onset of SUI can be months or years later, local chemokine production may have ceased, limiting the possibility of stem cell migration, retention, and repair. Failure of a therapeutic injection of MSCs is largely due to migration of locally injected cells away from the necessary site. Kean et al., Stem Cells Int. 2013, 732-742 (2013).

Among the chemokines known to serve as a chemoattractant when delivered together with MSC are CCR1, MIP-1, RANTES, SDF-1 and CCL7 (previously known as MCP-3). L. A. Marquez-Curtis, A. Janowska-Wieczorek, Biomed Res Int. 2013 561098 (2013). Of these, CCL7 is of particular importance in SUI treatment given evidence of its upregulation following vaginal trauma in different SUI animal models. For example, following vaginal distension, a rat model of birth trauma, CCL7 expression is significantly increased in rat urethral and vaginal tissues. Vricella et al., Urology. 76, 0-0 (2010); Wood et al., The Journal of Urology. 180, 753-759 (2008).

There is also precedent for the use of CCL7 as an MSC chemoattractant therapeutic agent in different injury scenarios. For example, in a rat model of heart ischemia, injection of hMSC showed preferential homing in mice overexpressing CCL7. Schenk et al., Stem Cells. 25 245-251 (2007). Osteogenic cells have also been show to preferentially migrate to fracture injuries of parabiotic co-joined mice containing CCL7 expressing MSC entrapped within a collagen matrix. Shinohara et al., J Orthop Res, 1064-9 (2011). In addition to differentiation and cellular repair, the therapeutic promise of autologous MSC treatment in the context of SUI also depends, in part, on MSC protein secretion when in contact with the injured tissue. Dissaranan et al., Cell Transplant. (Epub 2013) Likely, one reason some women fail to recover continence after birth trauma is due to a lack of a sufficient CCL7 concentration gradient to stimulate local MSC migration, induction of repair and tissue regeneration.

The inventors hypothesize that artificially increasing and sustaining local chemokine gradients will lead to MSC retention. To achieve sustained local concentrations of chemokine they relied on the affinity-based delivery of CCL7. Using polymers with a specific affinity toward a drug allows the capacity to reduce initial burst, and prolong the capacity of delivery beyond that capable of polymers using diffusion alone. Some of the earliest work in this space involved the use of sulfated proteoglycans and specific binding domains located in growth factors. Other groups have further demonstrated affinity-based release of cytokines using sulfated proteoglycans, most commonly heparin. The inventors were the first to show that this additionally be applied towards the new category of bioactive molecules: chemokines.

Affinity-based delivery polymers allow tailoring of drug release by properly selecting the strength of the affinity-binding element and by altering its amount in the matrix. N. X. Wang, H. A. von Recum, Macromol Biosci. 11, 321-332 (2011). Sulfated proteoglycans are known for their affinities to different chemokines by a combination of ionic, hydrophobic and hydrogen bonding molecular interactions. J. Shute, "Glycosaminoglycan and chemokine/growth factor interactions," Handb Exp Pharmacol. 307-324 (2012); Brandner et al., 22, 367-373 (2009). In this example, sulfated proteoglycans, as the affinity binding elements, were screened to determine the strength of the affinity towards CCL7. Polymers using proteoglycans with the strongest binding towards the chemokine were then synthesized and tested for their capacity to sustain local CCL7 gradients and MSC retention in the urethra of rats.

Materials and Methods

Surface Plasmon Resonance

The binding properties of recombinant CCL7 (R&D Systems) to several sulfated proteoglycans were analyzed by surface plasmon resonance on a BIACORE™ 3000 (GE Healthcare). CCL7 was conjugated to a CM5 chip (GE Healthcare) by activation with 0.4 M 1-ethyl-3-(3-dimethylpropyl)-carbodiimide (EDC, Fisher Scientific) and 0.1 M N-hydroxysuccinimide (NHS, Fisher Scientific) and subsequently blocked with 1M ethanolamine at pH 8.5 (Fisher Scientic). Heparin in the ranges of 12.5-250 nM (Invitrogen), heparan sulfate in the ranges of 1-20 μM (Invitrogen) or chondroitin sulfate in the ranges of 0.25-8 μM (Invitrogen) were individually tested to determine their dissociation constant ($K_D$). Dissociation constants were determined with the BIACORE™ evaluation software by fitting SPR data with a 1:1 affinity kinetics interaction between CCL7 and each of the proteoglcyans. The goodness of fit for the interaction model is measured by the Chi Square statistic. All SPR experiments yielding Chi square values below 10 were deemed acceptable for goodness of fit in Kd determination as per BIACORE™ specifications.

Polymer Synthesis

Three different types of polymer were assessed in this study: Heparin crosslinked with bovine serum albumin (BSA-H), Heparin crosslinked with poly(ethylene glycol) diamine (PEG-H), and "diffusion only" control polymers of BSA crosslinked without heparin(BSA). Heparin containing BSA polymers were synthesized as previously described by Wang. Briefly, BSA and heparin totaling 100 mg are crosslinked at a 25:75 or 100:0 ratio. Each heparin to BSA ratio was dissolved 0.1 M 2-(N-morpholino) ethanesulfonic acid (MES) at pH 5.2. Separately, 1 mg/ml of EDC in 0.1 M MES was prepared and mixed by vortexing with each 500 ul solution of heparin/BSA in a 15 mm scintillation vial (American Scientific). Polymers were cured overnight at room temperature, then removed from vials and rinsed 3 times in phosphate buffered saline (PBS). A 3 mm punch was used to cut consistent, cylindrical polymer disks.

Serum albumin was chosen as a ubiquitous biocompatible polyamine. However since there is a potential for immune response to bovine proteins in rats, and an expected foreign body response, we further evaluated affinity-based polymers made from poly(ethylene glycol) to take advantage of its capacity to resist protein and cell adhesion. Further we used this polymer to separate out any non-specific protein binding effects the BSA might have had on CCL7. For the PEG-H polymers a total of 50 mg of heparin was first completely dissolved in 150 μl of 0.1 M MES buffer. Next, 20 μg of NHS and 60 μg of EDC was added to the chilled heparin in MES solution and vortexed to ensure complete solubilization. Solutions were incubated on ice for 15 minutes and then PEG bisamine (mwt=2000) was dissolved in 100 μl of MES buffer. The PEG bisamine solution was mixed with heparin sodium/EDC/NHS solution and vortexed briefly. The reaction proceeded overnight at 4° C. Polymers were then washed, cut and dried as described above. For all experiments polymers were rehydrated for 48 hrs in 300 μl of PBS with or without 200 μg/ml of CCL7.

Release Kinetics

Drug release profiles for each of the polymers were determined in vitro. Each polymer disk was bathed in release solution (1 mL of 0.1% BSA in PBS) at 37° C. under gentle agitation. CCL7 release from BSA-based polymers was evaluated in triplicate for each condition. Release from PEG-H polymers was similarly performed, in duplicate. Infinite sink conditions were generated by sampling daily for the first 2 weeks, followed by sampling every other day for a total of 4 weeks. Polymers were removed from conditioned release solution and placed into fresh release buffer at each time point. Samples of conditioned release solution were stored at −20° C. for later analytical quantification of the CCL7 by ELISA. CCL7 ELISA kit (R&D Systems) measured protein for each aliquot as per the manual. Results are reported as the average concentration and the cumulative release for each time point.

Polymer Implants in Rats

To evaluate the anatomical feasibility and biocompatibility of affinity-based polymers in vivo, CCL7 containing polymers were implanted into female Sprague-Dawley (SD) rats peri-urethrally. Specifically implants went beneath the epithelium and within the anterior vaginal wall alongside the urethra. After three weeks the vaginal and urethral tissue was harvested. The vagina was cut longitudinally from the posterior wall and the interior side of the vaginal lumen was exposed to identify the implanted polymer.

CCL7 Tissue Distribution

Nine female SD rats were implanted with approximately 20 mg of each different polymer formulation and divided into three groups of three. The first group was given BSA-H polymers with CCL7 (BSA-H-C7) surgically implanted while a second group received PEG-heparin with CCL7 (PEG-H-C7). The control group received BSA-heparin polymers without CCL7 (BSA-H). Serum samples were collected at 5, 7, 10 and 12 days. Fourteen days after implantation the rats were sacrificed and urethral tissue adjacent to anterior wall of vagina and in the direct vicinity of the polymer was harvested from each animal. The tissue was immediately snap frozen in liquid nitrogen and stored it at −80° C. until CCL7 measurements from tissue were carried out by ELISA as above. Serum content of CCL7 was also determined by ELISA.

hMSC Cell Culture

Human mesenchymal stem cells from a single donor source, kindly provided by Dr. Arnold Caplan, CWRU, were expanded in high glucose DMEM supplemented with 10% FBS. Cells used in fluorescent cryoimaging experiments cells were labeled with Lavacell™ (Active Motif, CA) as per manufacturer's instructions.

Imaging of Injected hMSC

Visualization of hMSC retention in response to exogenous CCL7 in vivo was done by implanting female SD rats with either BSA-H polymers with CCL7 or without CCL7 as described above. At day 12 post-implantation rats were periurethrally injected with $1.5*10^6$ LAVACELL™ labeled hMSCs in 100 μl PBS. Animals were sacrificed 24 hours after injection, preserved in cryo-embedding Optimal Cutting Temperature compound (TISSUE-TEK™, Terrance, Calif.), frozen in liquid nitrogen, and stored at −80° C. prior to sectional imaging. Cryo-preserved animals were sectioned at a 40 mm in thickness with an automatic cryo-microtome capable of simultaneous sectioning and imaging (BIOINVISION™, OH).

Results

Surface Plasmon Resonance

Figure 11:
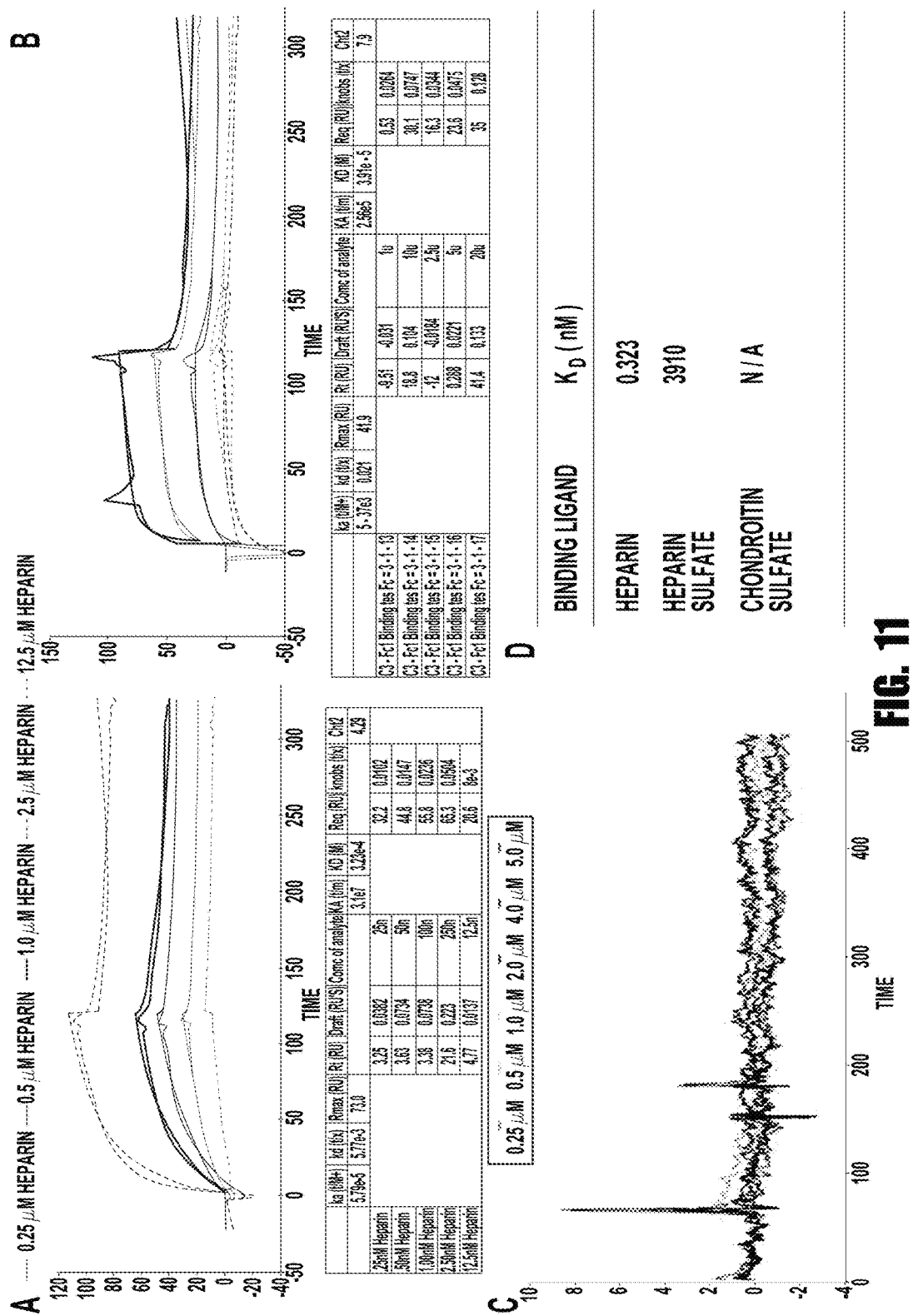

Binding affinity of CCL7 was determined for heparin, heparin sulfate, or chondroitin sulfate. At 32.3 nM CCL7 affinity for heparin was greater than that for heparin sulfate (3900 nM) or chondroitin sulfate (which was undetectable even at the micromolar range). Characteristic saturation curves after injection of the proteoglycans was observed in sensorgrams (FIG. 11). No upper limit of saturation for heparin or heparin sulfate was identified. SPR experiments yielded chi square values less than 10 for all conditions.

Release of CCL7 In Vitro

CCL7 release profiles under infinite sink conditions were determined for each polymer formulation in this study. The amount of CCL7 present in each aliquot at each time point as well as calculated the total cumulative release of CCL7 was assessed to determine if the release rate was within the observed bioactive range of the chemokine. A cumulative CCL7 peaked at day 4 in BSA-H polymers while BSA-H-C7 polymers continued to release CCL7 for up to 14 days (FIG. 12A). The lowest cumulative CCL7 release was observed in the PEG-H polymers which showed no evidence of reaching saturation, slowly releasing drug for the duration of the experiment (FIG. 12A). Sustained CCL7 release was observed for the duration of the experiment for both affinity conditions for up to a month of release. Both PEG-H-C7 and BSA-H-C7 polymers lacked an initial rapid release as it was observed in the BSA-C7 polymers. FIG. 12b. After 29 days, a statistically significant difference in CCL7 release between heparin containing polymers and heparin free polymers could be detected (FIG. 12b). By day 29 polymers containing heparin released 5-fold more CCL7 per day than heparin free controls FIG. 12b. The CCL7 content in heparin free controls was rapidly depleted and as expected at later time points released less CCL7 protein ($10^1$ pg). By day 30 a total of 5.2 μg of protein was released from BSA-C7 polymers, BSA-H-C7 polymers released 3.5 μg of protein and PEG-H—C7 polymers released 0.75 μg of protein.

Polymer Implantation

At three weeks, to evaluate the physiological impact and feasibility of intra pelvic CCL7 polymer therapy, implanted polymers were extracted from the vaginal epithelium and any gross pathology observed was noted. Polymers remained in place for the duration of the experiment and lacked shifts due to animal motion. Particular note was made of the local tissue response to the implants. A fibrous capsule containing seemingly sterile purulent material surrounded the BSA and BSA-H polymers. Due to the purulent materiel, the BSA-heparin polymers were easily extracted from the surrounding capsule. This response was also present in BSA polymers with and without heparin, FIGS. 13A and 13B. Purulent infiltrate was not present within the fibrous capsule surrounding the PEG polymer. Further, the fibrous capsule was firmly adherent to the PEG polymer and difficult to excise FIGS. 13C and 13D.

CCL7 Tissue Distribution

Figure 14:
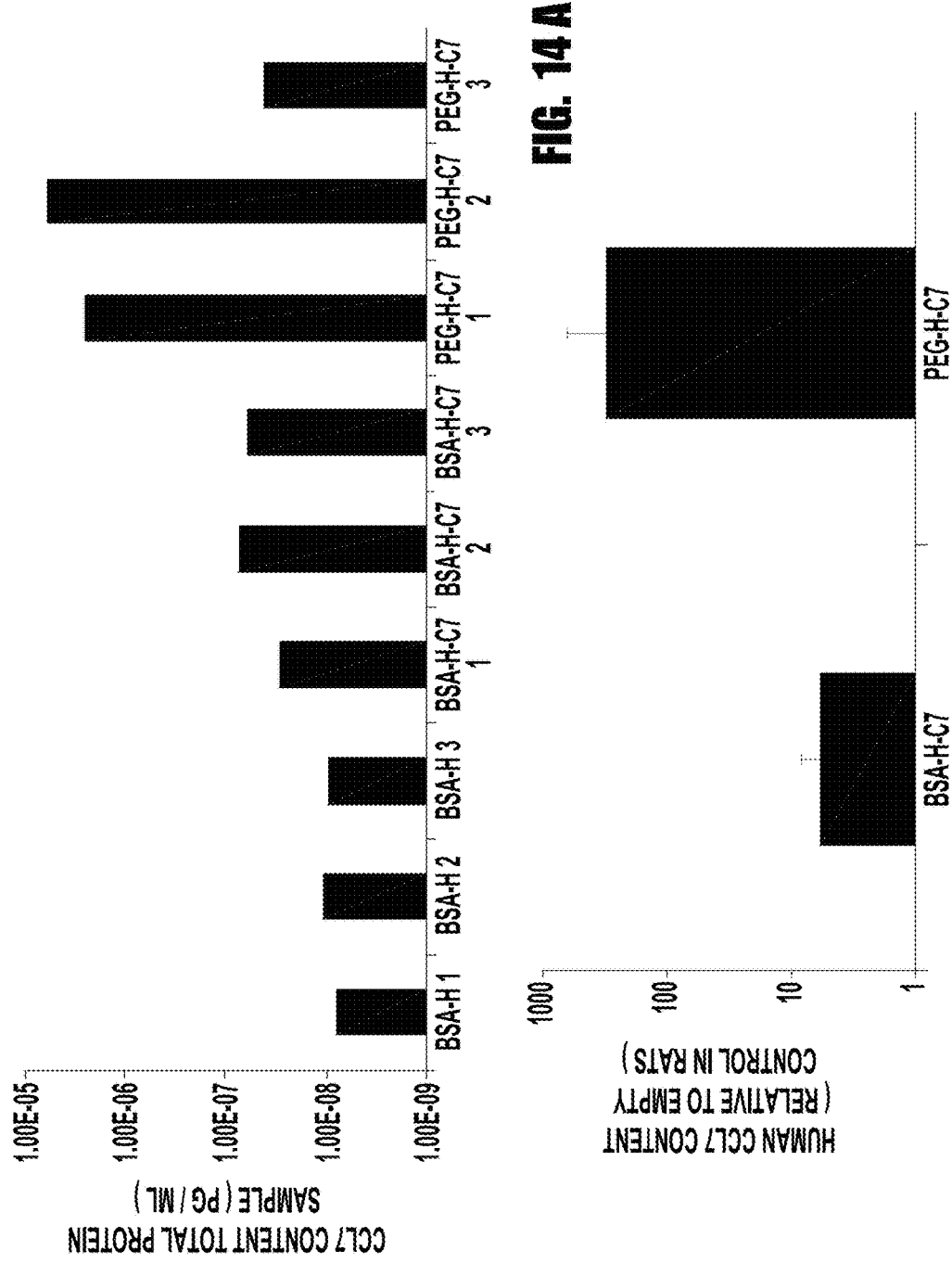

To test the CCL7 distribution from the polymer delivery in vivo the tissue directly surrounding the urethra was harvested at day 14. Serum samples were obtained from animals at different time points post implantation (day 5, 7, 10 and 12). Human serum CCL7 concentration was below the assays level of detection in all conditions. Human CCL7 was undetectable in unloaded BSA-H polymers. For comparison purposes unloaded BSA-H polymers were set as a normalization variable for the other conditions. (FIG. 14A). Human CCL7 was detected above background for both heparin containing BSA and PEG polymers a range from 5 to 300 times the values detected in unloaded BSA-H polymers (FIG. 14B). Logarithmically transformed mean urethral tissue CCL7 concentrations were significantly different between BSA, BSA-H-C7, and PEG-H-C7 polymer implanted animals by ANOVA (p value=0.03). A post-hoc Tukey test analysis determined a statistically significant difference between PEG-H-C7 and unloaded BSA-H with weak evidence of a difference between BSA-H-C7 polymers above BSA-H.

Stem Cell Retention In Vivo

Figure 15:
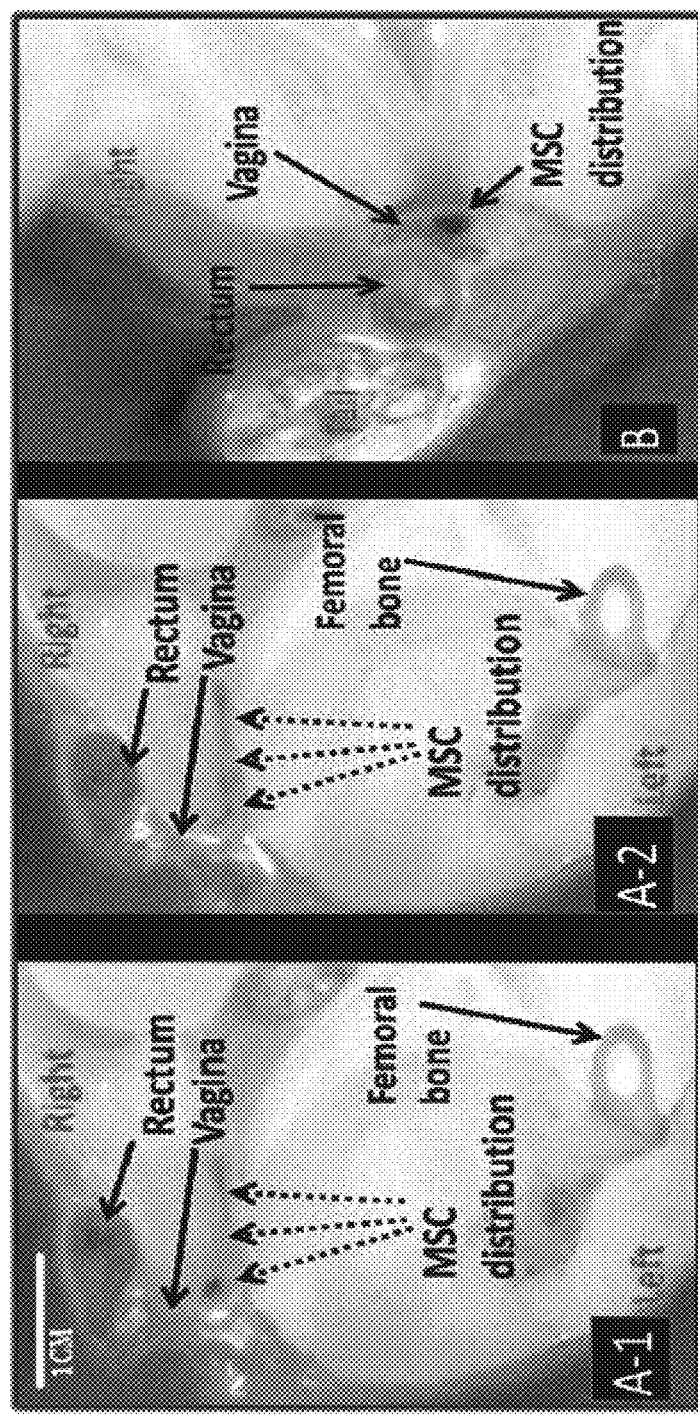

Pro-migratory and homing responses of LAVACELL™ labeled hMSC to local CCL7 concentration gradients was assessed in CCL7 containing polymers by whole body fluorescent imaging of 40 μm sections. BSA-H polymer implanted animals were compared to BSA-H-C7 polymer implanted animals. The inventors characterized hMSC identified in fluorescent images from empty BSA-H polymers as having a diffuse distribution pattern radiating away from the injection site with lower LAVACELL™ signal intensity FIGS. 15 A-1 and 15 A-2. BSA-heparin polymers loaded with CCL7 showed a localized and high intensity fluorescent signal at the injection site and lacked diffusive distribution away from the injection FIG. 15B.

Figure 16:
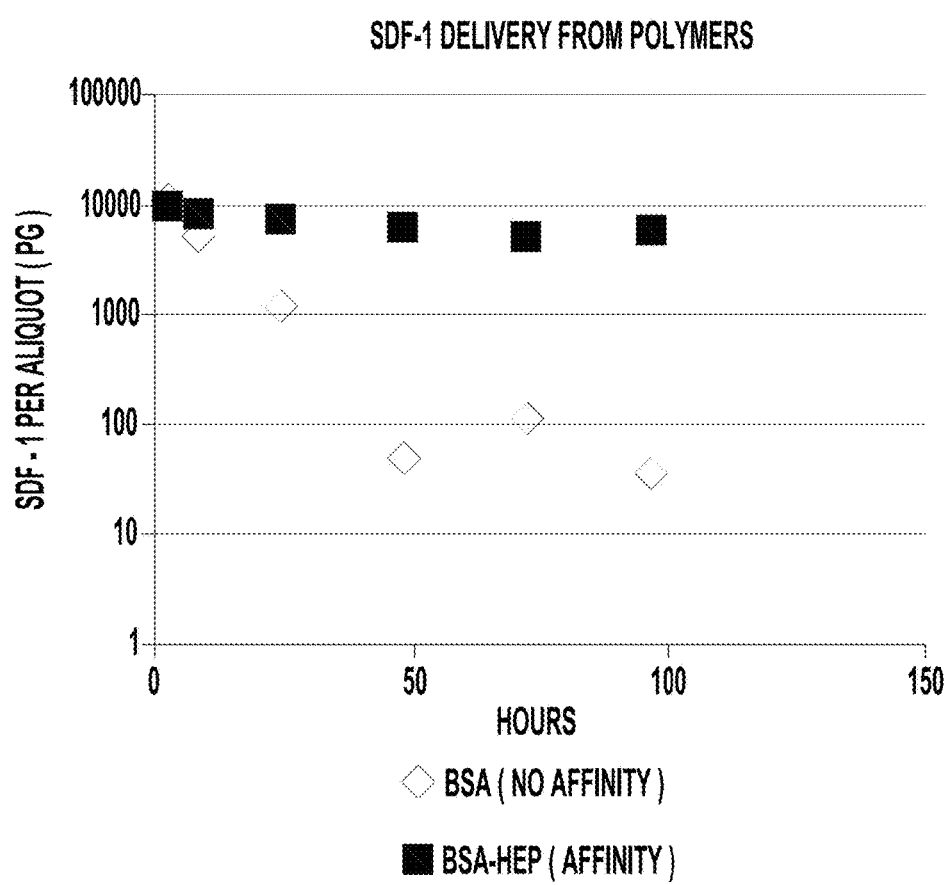
FIG. 16 provides a graph showing delivery of CXCL12 (MCP-3) from a polymer bearing heparin, providing ~2 orders of magnitude greater regular dose than polymer with no heparin.

In an additional experiment carried out using CXCL12, it was shown that delivery of CXCL12 (MCP-3) from a polymer bearing heparin provided ~2 orders of magnitude greater regular dose than polymer with no heparin. See FIG. 16.

Discussion

Figure 13:
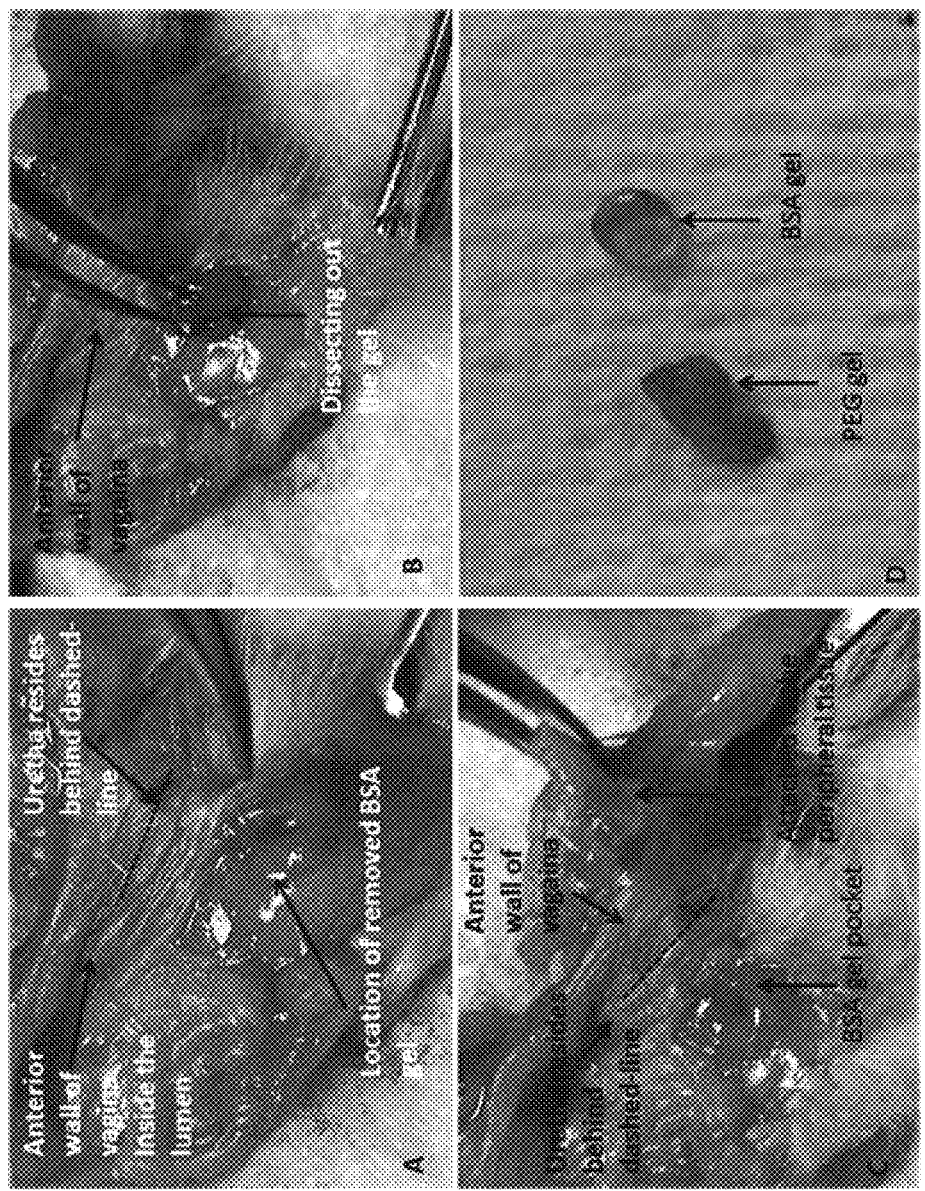

The inventors demonstrate long-term human CCL7 delivery can be achieved by the proper selection of an affinity-binding ligand and such extended release increases hMSC retention in the vaginal tracts of rats. An affinity between CCL7 and heparin was observed in SPR studies and a Kd of 0.323 nM (FIG. 11) was determined. The in vivo utility of BSA-H-C7 polymers is reasonable considering our observation of a 4-fold increase in the total available CCL7 released over the period of a month. (FIG. 12B). Sustained in vitro release of CCL7 translated to higher tissue CCL7 concentrations in animals implanted with either PEG-H-C7 or BSA-H-C7 affinity polymers (FIG. 13). Extended local delivery of CCL7 caused hMSC injected peripherally to the polymer to coalesce in the direction of implantation (FIG. 15C) while hMSC, in the absence of implants with CCL7, radiated outward from the injection site (FIG. 15A).

To engineer biomaterials capable of sustained drug delivery, understanding the complex ligand and chemokine interaction is critical. The inventors determined this affinity interaction for CCL7 to three different sulfated proteoglycans known to bind chemokines. Heparin had the highest affinity towards CCL7 and consequentially the longer sustained release of CCL7 when crosslinked into an insoluble CCL7 releasing polymer. These findings go in accordance with the delayed and prolonged release of chemokines when affinity interactions are in the nanomalor region described in Example 1. Despite similar polymer content and loading concentrations the depletion of CCL7 from polymers is significantly slower in the presence of heparin. This validates our expectation an affinity molecule will substantially delay the release of a bound ligand.

The polymeric backbone material also affected cumulative release in this study. This is understandable since properties, such as polymer network hydrodynamic radius, polymer swelling and network elasticity will also contribute to the overall rate release as shown by the PEG-H-C7 release data. Nevertheless, holding everything else equal the rate release of more physically similar polymers should be modulated by the strength of the affinity between the ligand and the interacting molecules. Fu et al., Ann Biomed Eng. 39, 2466-2475 ((2011). PEG-H-C7 were included in this experiment to take into account the inflammatory response elicited by the BSA portion of the polymers.

Affinity bound polymers also substantially increased the local concentration of CCL7 when compared to vehicle alone. Unexpectedly, local concentration of CCL7 from BSA-H-C7 was lower than PEG-H-C7 polymers. The cumulative release kinetics data predicted greater total cumulative release from the BSA-heparin polymers. However, this prediction did not anticipate a strong immune response to the BSA-heparin as observed in vivo. Likely, CCL7, acting as a potent chemoattractant and BSA, composed of non-self proteins, stimulated a potent immune reaction. This is consistent with the purulent capsule we noted around the BSA and BSA-H-C7 implanted polymers. In contrast, PEG-heparin-CCL7 polymers formed a fibrous and integrated capsule. The complex cytokine mixture and cell types involved in pustule formation likely mask increased CCL7 release from the BSA-H-CCL7 polymers and could explain reduced local CCL7 concentration. The lack of significant presence of CCL7 in the bloodstream of the animals rules out the possibility of convective clearance of CCL7 to the blood compartment. One must therefore also conclude another important factor in the design of implantable drug delivery systems is the kinetics of immune response to the combination of polymer, ligand, and macromolecule.

These findings are significant to the fields of drug delivery, SUI treatment and therapeutical delivery of MSC. The cryoimaging data support previous observations by Schenk and others of hMSC chemo-attraction in response to CCL7. Schenk et al., Stem Cells. 25 245-251 (2007). Additionally, an affinity-based drug delivery system capable of sustained CCL7 release and recruitment of exogenously implanted hMSCs has been developed. Despite the presence of a chemoattractant gradient it may be possible for this gradient to rapidly subside or not be present at all at the time of clinical intervention. This method is further complicated by the short half-life of chemokines in the blood and interstitial tissue. Adopting a strategy to boost the local concentration of pro-homing chemokines could eliminate three major MSC delivery related problems. First, it would allow screening for chemokines capable of improving the extent of MSC homing and retention in vivo. Second, it would allow controlled expression of homing and retention chemokines throughout injury repair. Third, it would allow induction of MSC homing and retention behavior in the absence of injury as is observed in the majority of women who need surgical intervention for SUI.

CONCLUSIONS

The goal of this research was to demonstrate hMSC retention is possible with sustained increased local CCL7 concentration. Retention of labeled hMSC was observed in the injection site of rats with CCL7 impregnated polymers.

Affinity delivery of bioactive molecules is an effective long-term drug delivery strategy. This example describes the use of these molecular interactions in a matrix type system to deliver the chemokine CCL7 in rats. CCL7 has been recently implicated in the recruitment of MSC's in different sites of injuries. This work expands upon these findings by providing a delivery route for CCL7 type chemokines in the context of SUI. It is likely that other chemokines, such as SDF-1 and MIP-1 which are involved in the recruitment, homing and survival of therapeutic MSC show an affinity for sulfated proteoglycans. Affinity delivery of these other chemokines may prove to be useful by protecting the chemokines from degradation and maintaining bioactive concentrations in the optimal timeframe of treatment.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A pharmaceutical composition for sustained release of a chemokine, comprising a polymer bonded to a sulfated glycosaminoglycan and associated with a chemokine selected from chemokine (C-C motif) ligand 3 (CCL3), chemokine (C-C motif) ligand 4 (CCL4), chemokine (C-C motif) ligand 5 (CCL5), chemokine (C-C motif) ligand 7 (CCL7), Regulated on Activation, and Normal T Expressed and Secreted 5P12 analog (5P12-RANTES), wherein the polymer is included in a preformed device designed to fit within a cavity in the body, and wherein the preformed device is not microspheres.

2. The pharmaceutical composition of claim 1, wherein the preformed device is a polymeric ring.

3. The pharmaceutical composition of claim 1, wherein the polymer is a hydrogel.

4. The pharmaceutical composition of claim 1, wherein the polymer comprises bovine serum albumin.

5. The pharmaceutical composition of claim 1, wherein the polymer is crosslinked with a plurality of types of sulfated glycosaminoglycans.

6. The pharmaceutical composition of claim 1, wherein one or more of the sulfated glycosaminoglycans are selected from the group consisting of heparin, chondroitin sulfate A, and chondroitin sulfate B.

7. The pharmaceutical composition of claim 5, wherein the chemokine is CCL5.

8. The pharmaceutical composition of claim 5, wherein the chemokine is CCL7.

9. A method for providing sustained release of a chemokine to a subject, comprising contacting the subject with a pharmaceutical composition according to claim 1.

10. The method of claim 9, wherein the preformed device is a polymeric ring.

11. The method of claim 9, wherein the polymer is a hydrogel.

12. The method of claim 9, wherein the polymer comprises bovine serum albumin.

13. The method of claim 9, wherein the polymer is crosslinked with a plurality of types of sulfated glycosaminoglycans.

14. The method of claim 9, wherein one or more of the sulfated glycosaminoglycans are selected from the group consisting of heparin, chondroitin sulfate A, and chondroitin sulfate B.

15. The method of claim 14, wherein the chemokine is CCL5.

16. The method of claim 14, wherein the chemokine is CCL7.

* * * * *